(12) United States Patent
Brem et al.

(10) Patent No.: US 10,351,525 B2
(45) Date of Patent: Jul. 16, 2019

(54) BETA LACTAMASE INHIBITORS

(71) Applicant: Oxford University Innovation Limited, Oxford (GB)

(72) Inventors: Jürgen Brem, Oxford (GB); Sander S. Van Berkel, Oxford (GB); Michael A. McDonough, Oxford (GB); Christopher J. Schofield, Oxford (GB)

(73) Assignee: Oxford University Innovation Limited, Botley, Oxford (GB)

( * ) Notice: Subject to any disclaimer, the term of this patent is extended or adjusted under 35 U.S.C. 154(b) by 0 days.

(21) Appl. No.: 15/516,096

(22) PCT Filed: Sep. 18, 2015

(86) PCT No.: PCT/GB2015/052705
§ 371 (c)(1),
(2) Date: Mar. 31, 2017

(87) PCT Pub. No.: WO2016/051133
PCT Pub. Date: Apr. 7, 2016

(65) Prior Publication Data
US 2017/0369433 A1    Dec. 28, 2017

(30) Foreign Application Priority Data
Oct. 3, 2014  (GB) .................. 1417529.3

(51) Int. Cl.
| | |
|---|---|
| *A61K 31/192* | (2006.01) |
| *A61K 31/426* | (2006.01) |
| *A61K 31/496* | (2006.01) |
| *C07C 323/52* | (2006.01) |
| *A61K 31/095* | (2006.01) |
| *C07D 277/36* | (2006.01) |
| *C07C 323/56* | (2006.01) |
| *C12Q 1/34* | (2006.01) |

(52) U.S. Cl.
CPC .......... *C07C 323/52* (2013.01); *A61K 31/095* (2013.01); *A61K 31/192* (2013.01); *A61K 31/426* (2013.01); *A61K 31/496* (2013.01); *C07C 323/56* (2013.01); *C07D 277/36* (2013.01); *C12Q 1/34* (2013.01); *C12Y 305/02006* (2013.01); *G01N 2333/986* (2013.01); *Y02A 50/473* (2018.01)

(58) Field of Classification Search
CPC ... A61K 31/192; A61K 31/426; C07C 323/52
See application file for complete search history.

(56) References Cited

U.S. PATENT DOCUMENTS

| | | |
|---|---|---|
| 4,169,149 A | 9/1979 | Giroux et al. |
| 4,439,443 A | 3/1984 | Giroux |
| 5,760,048 A | 6/1998 | Wang et al. |
| 7,807,403 B2 | 10/2010 | Black et al. |
| 8,097,434 B2 | 1/2012 | Yang-Woytowitz et al. |
| 2002/0019543 A1 | 2/2002 | Balkovec et al. |

FOREIGN PATENT DOCUMENTS

| | | |
|---|---|---|
| EP | 0779554 | 6/1997 |
| WO | WO 2010/111504 | 9/2010 |
| WO | WO 2013/015456 | 1/2013 |
| WO | WO 2013/063204 | 5/2013 |
| WO | WO 2016/051133 | 7/2016 |

OTHER PUBLICATIONS

Adams et al., "Potent Inhibition of $Ca^{2+}$-Dependent Activation of Calpain-1 by Novel Mercaptoacrylates," Med. Chem. Commun. 3: 566-570 (2012).
Barreiro et al., "Synthesis and Antimicrobial Activities of Gold(1) Sulfanylcarboxylates," *Gold Bulletin*. 45(1): 23-34 (2012).
Barreiro et al., "Synthesis and Antimicrobial Activities of Silver(I) 3-(substituted phenyl) Sulfanylpropenoates," *European Journal of Medicinal Chemistry*. 42(11): 2489-2497 (2008).
Betts et al., "In Vitro and in Vivo Activity of ML302F: A Thioenolate Inhibitor of VIM-Subfamily Metallo B-Lactamses," Med. Chem. Commun. DOI: 10.1039/C5MD00380F (2015).

(Continued)

*Primary Examiner* — Zohreh A Fay
(74) *Attorney, Agent, or Firm* — Hamilton, Brook, Smith & Reynolds, P.C.

(57) ABSTRACT

A compound which is a thienolate of formula (I) or a pharmaceutically acceptable salt thereof: (I) wherein $R^1$, $R^3$, Ring A1, n and Ring A2 are as defined herein, are found to be useful in inhibiting metallo-beta-lactamase and therefore in potentiating the activity of beta lactamase antibiotics. The compound can be used alone or in combination with a rhodanine of formula (II) or a pharmaceutically acceptable salt thereof: (II) wherein $R^3$, Ring A1, n, Ring A2, L and Ring B are as defined herein. Treatment or prevention of bacterial infection in combination with beta-lactam antibiotic agents is also provided.

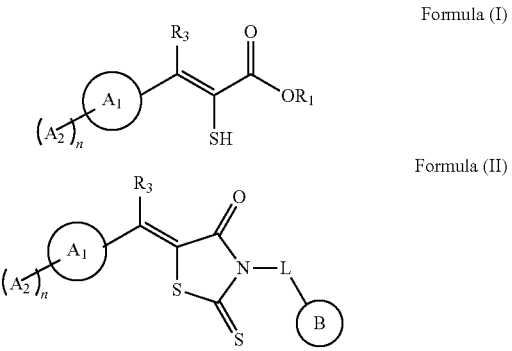

Formula (I)

Formula (II)

21 Claims, 2 Drawing Sheets

(56) References Cited

OTHER PUBLICATIONS

Brem et al., "Rhodanine Hydrolysis Leads to Potent Thioenolate Mediated Metallo-β-Lactamase Inhibition," Nature Chemistry. 12(6): 1084-1090 (2014).
Campaigne & Cline, "Preparation and Absorption Spectra of Some p-Aryl-a-Mercaptoacrylic Acids and Related Disulfides," J. Org. Chem. 21: 32-38 (1956).
Casas et al., "Chemical and in vitro study of the potential of 3-(aryl)-2-sulfanylpropenoic acids and their Zn(n) complexes as protective agents against cadmium toxicity," Dalton Trans. 39 : 3931-3943 (2010).
Casas et al., "Triphenyltin(IV) sulfanylpropenoates: synthesis, crystal structures and antimicrobial activities," Applied Organometallic Chemistry. 14(8): 421-431 (2000).
Hammond et al., "Inhibition of IMP-1 Metallo-β-Lactamase and Sensitization of IMP-1-Producing Bacteria by Thioester Derivatives," FEMS Microbiology Letters, 179(2): 289-296 (1999).
Haskell et al., "Neuraminidase Inhibition and Viral Chemotherapy," Journal of Medicinal Chemistry. 15(4): 697-704 (1970).
Hornsey and Wareham, "In Vivo Efficacy of Glycopeptide-Colistin Combination Therapies in a Galleria Mellonella Model of Acinetobacter Baumannii Infection," Antimicrob. Agents Chemother. 55(7): 3534-3537 (2011).
International Search Report and Written Opinion for International Application No. PCT/GB2015/052705, "Beta Lactamase Inhibitors" dated Apr. 4, 2017, consisting of 7 pages.
Jensen et al., "Enethtols X,* About 2-Mercapto-Cinnamic Acids," Bulletin De La Société Chimique Belge. 86(8): 639-646 (1977).
King et al., "Aspergillomarasmine A Overcomes Metallo-b-Lactamase Antibiotic Resistance," Nature. 510(7506): 503-506 (2014).
Liénard et al., "Structural Basis for the Broad-Spectrum Inhibition of Metallo-P-Iactamases by Thiols," Organic and Biomolecular Chemistry. 6: 2282-2294 (2008).
Lin et al., "Crystal Structure of Calcium Bound Domain VI of Calpain at 1.9 a Resolution and Its Role in Enzyme Assembly, Regulation, and Inhibitor Binding," Nature Structural Biology. 4(7): 539-547 (1997).
Makena et al., "Chromophore-Linked Substrate (CLS405): Probing Metallob-Lactamase Activity and Inhibition," Chem MechCHem. 8(12): 1923-9 (2013).
Matsui, "Mechanism of Formation of a,p-Unsaturated Esters in the Reaction of Ethyl Mercaptoacetate Dianion with Carbonyl Compounds," Bulletin of Chemical Society of Japan. 57(2): 426-434 (1984).
Metwally, "3-Aryl-2-Sulfanylpropenoic Acids As Precursors for Some Novel (Z)-5-Substituted-2-Alkoxy-2-Trichloromethy1-4-Thiazolidinones," Arkivoc. X: 254-265 (2011).
Mollard et al., "Thiomandelic Acid, a Broad Spectrum Inhibitor of Zinc-Lactamases," J. Biol. Chem. 2476: 45015-45023 (2001).
Notification Concerning Transmittal of International Preliminary Report on Patentability for International Application No. PCT/GB2015/052705, "Beta Lactamase Inhibitors", dated Apr. 13, 2017.
Ogawa et al., "Imidase, A Dihydropyrimidinase-Like Enzyme Involved in the Metabolism of Cyclic Imides," Eur. J. Biochem. 243: 322-327 (1997).
Omar et al., "The Route of Action of Sodium Methoxide on 5-Arylmethylene-2-Disubstituted Amino-4-oxo-2-thiazolines," Journal of Heterocyclic Chemistry. 18: 1413-1415 (1981).
Pelto, et al., "Kinetics and Stereochemistry of Hydrolysis of an N-(Phenylacetyl)-A-Hydroxyglycine Ester Catalyzed by Serine B-Lactamases and DD-Peptidases," Org. Biomol. Chem. 10: 7356-7362 (2012).
Rahman et al., "7-Substituted Benzo[b]thiophenes and 1,2-Benzisothiazoles. Part 2. 1 Chloro and Nitro Derivatives," J. Chem. Soc. Perkin Trans. 1: 385-390 (1984).
Search Report for GB Application No. GB1417529.3, "Beta Lactamase Inhibitors", dated Jun. 17, 2015.
Spicer et al., "ML302, a Novel Beta-lactamase (BLA) Inhibitor ," Probe Reports from the NIH Molecular Libraries Program. National Center for Biotechnology Information (US) Bethsada (MD) (2010).
Van Berkel et al., "Assay Platform for Clinically Relevant Metallo-β-lactamases," J. Med. Chem. 56: 6945-6953 (2013).
Van Berkel et al., "Binding of (55)-Penicilloic Acid to Penicillin Binding Protein 3," ACS Chem. Biol. 8(10): 2112-2116 (2013).
Wang et al., An alpha-mercaptoacrylic acid derivative is a selective nonpeptide cell-permeable calpain inhibitor and is neuroprotective (1996) Proc. Natl. Acad. Sci. USA. 93(13): 6687-6692 (1996).
Yamaguchi et al., "crystallographic Investigation of the Inhibition Mode of a VIM-2 Metallo-β-lactamase from Pseudomonas aeruginosa by a Mercaptocarboxylate Inhibitor", (2007) J. Med. Chem. 50: 6647-6653.
Zhanel et al., "Ceftazidime-Avibactam: a Novel Cephalosporin/b-lactamase Inhibitor Combination," Drugs. 73(2): 159-177 (2013).

BETA LACTAMASE INHIBITORS

This application is the U.S. National Stage of International Application No. PCT/GB2015/052705, filed Sep. 18, 2015, which designates the U.S., published in English, and claims priority under 35 U.S.C. §§ 119 or 365(c) to Great Britain Application No. 1417529.3, filed Oct. 3, 2014. The entire teachings of the above applications are incorporated herein by reference.

FIELD OF THE INVENTION

The invention relates to compounds for use in the inhibition of bacterial metallo-beta-lactamases. The compounds are therefore useful in potentiating the effects of β lactam antibiotic agents and can be used in combination with β lactam antibiotic agents in the prevention and treatment of bacterial infection. Compounds and combinations useful in these methods are also provided.

BACKGROUND TO THE INVENTION

The β-lactams remain the most widely used antibiotics and are consequently amongst the most important medicines in current use. β-Lactam antibiotics inhibit transpeptidases (penicillin binding proteins, PBPs) involved in cell wall biosynthesis by reacting with a nucleophilic serine-residue important in catalysis. The use of β-lactams is compromised by resistance mechanisms, including by the action of β-lactamases (BLs), which catalyse β-lactam hydrolysis. Four classes of BLs have been identified on the basis of substrate selectivity and structure. Classes A, C and D are 'serine' BLs and are evolutionarily and mechanistically related to the PBPs. Class B BLs are zinc dependent hydrolases that are mechanistically distinct.

Inhibitors of the Class A enzymes ('penicillinases'), i.e. clavulanic acid, tazobactam, and sulbactam, have been developed and have substantially extended the spectrum of activity of otherwise Class A BL susceptible partner penicillins. Inhibitors of the Class C BLs ('cephalosporinases') are also being developed with one, Avibactam (NXL-104), being in late stage clinical trials. Moreover, Avibactam also targets Class A and some Class D enzymes, but not Class B MBLs. As yet, however, there are no reports of clinically useful inhibitors of the Class B metallo-BLs (MBLs).

MBLs are an increasing clinical concern since they catalyse the hydrolysis of almost all β-lactam antibiotics. Based on the number of Zn ions in their active site and sequence/structural similarities, MBLs can be subdivided into three subclasses (B1, B2 and B3). MBLs belonging to the B1 subclass are presently considered to be the most clinically relevant (e.g. IMP—Imipenemase, VIM—Verona integron-encoded MBL, and NDM—New Delhi MBL types) since they inactivate almost all BLs, including the latest generations of cephalosporins and all carbapenems, which are often considered "last resort antibiotics". The potential threat of MBLs is highlighted by NDM-1, which enables resistance in many pathogenic strains. Further, an increasing number of organisms containing both serine BLs (SBLs) and MBLs are being reported. There is thus a need to develop not only MBL inhibitors, but compounds with dual SBL and MBL inhibition properties for use in combination therapies.

SUMMARY OF THE INVENTION

The present invention provides a compound which is a thienolate of formula (I) or a pharmaceutically acceptable salt thereof, for use in a method of inhibiting bacterial metallo-beta-lactamase:

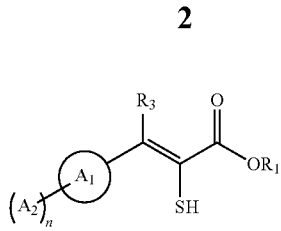

Formula(I)

wherein
$R^1$ is H or a $C_1$ to $C_4$ alkyl group;
$R^3$ is H, halogen, $C_1$ to $C_4$ alkyl, $C_1$ to $C_4$ alkoxy, $C_2$ to $C_4$ alkenyl, or —$NR^4R^5$; Ring A1 is a $C_6$ to $C_{10}$ aryl or 5- to 10-membered heteroaryl group which is unsubstituted or substituted with from 1 to 4 substituents selected from halogen, OH, —$NR^4R^5$, CN, $NO_2$, —$C(O)R^4$, —$C(O)OR^4$, —$C(O)NR^4R^5$, —$S(O)R^4$, and from $C_1$ to $C_4$ alkyl, $C_1$ to $C_4$ alkoxy and $C_2$ to $C_4$ alkenyl groups which are themselves unsubstituted or substituted with from 1 to 3 further unsubstituted substituents selected from halogen, OH, —$NR^4R^5$ and $C_1$ to $C_4$ alkoxy;
n is 0 or 1;
Ring A2 is a $C_6$ to $C_{10}$ aryl or 5- to 10-membered heteroaryl group which is unsubstituted or substituted with from 1 to 4 substituents selected from halogen, OH, —$NR^4R^5$, CN, $NO_2$, —$C(O)R^4$, —$C(O)OR^4$, —$C(O)NR^4R^5$, —$S(O)R^4$, and from $C_1$ to $C_4$ alkyl, $C_1$ to $C_4$ alkoxy and $C_2$ to $C_4$ alkenyl groups which are themselves unsubstituted or substituted with from 1 to 3 further unsubstituted substituents selected from halogen, OH, —$NR^4R^5$ and $C_1$ to $C_4$ alkoxy; and
$R^4$ and $R^5$ each independently represent H or $C_1$ to $C_4$ alkyl.

The compounds described above have surprisingly been found to be broad spectrum metallo-beta-lactamase (MBL) inhibitors. They are therefore useful in methods of inhibiting MBL.

DETAILED DESCRIPTION OF THE INVENTION

Figure 1:
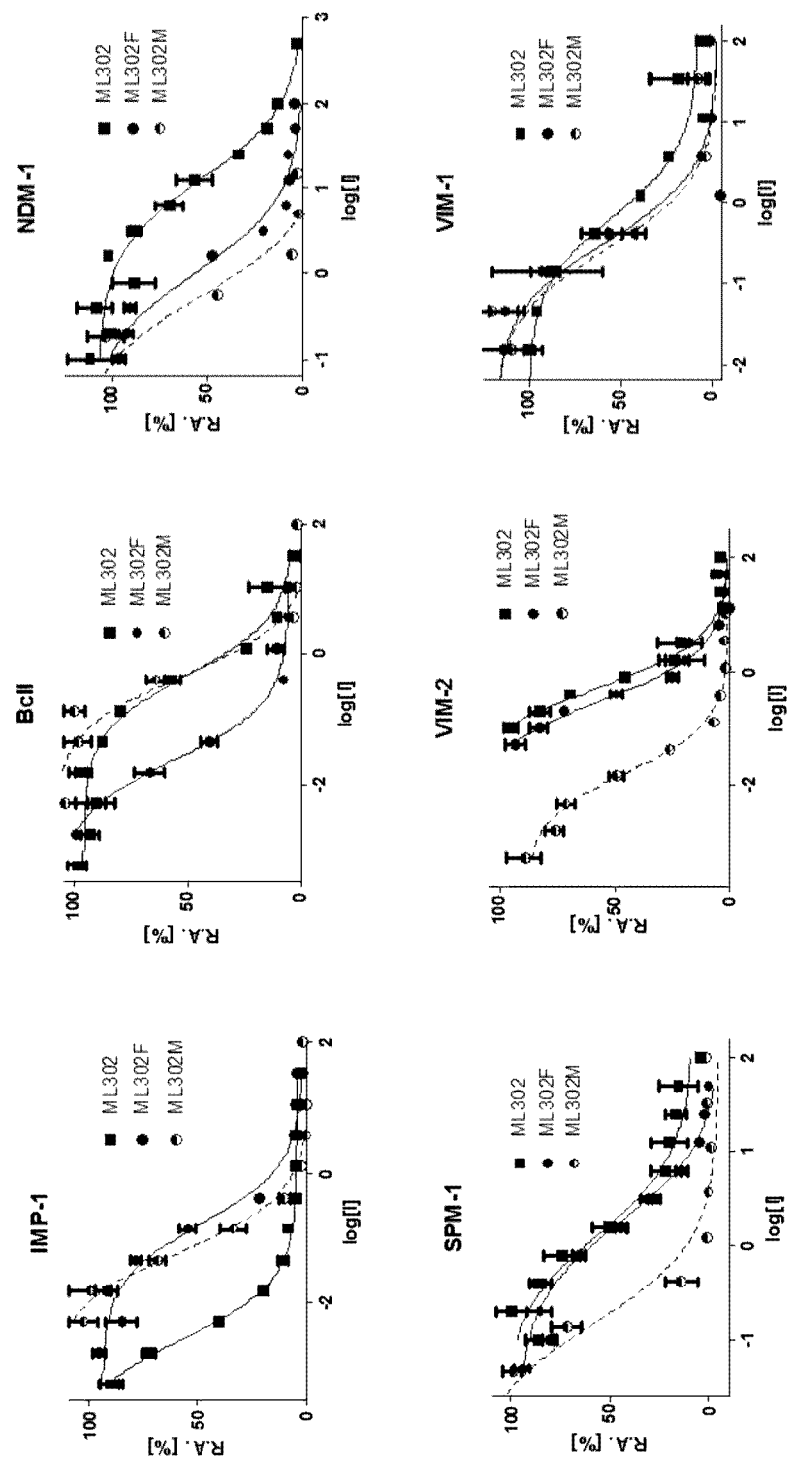
FIG. 1 provides $IC_{50}$ curves for a compound and combination as described herein for a panel of MBLs.

As used herein, a $C_1$ to $C_4$ alkyl group is a linear or branched alkyl group containing from 1 to 4 carbon atoms. Examples of $C_1$ to $C_4$ alkyl groups include methyl, ethyl, n-propyl, iso-propyl, n-butyl, sec-butyl and tert-butyl. A $C_1$ to $C_4$ alkyl group is typically a $C_1$ to $C_2$ alkyl group, i.e. methyl or ethyl, typically methyl. For the avoidance of doubt, where two alkyl groups are present, the alkyl groups may be the same or different.

As used herein, a $C_2$ to $C_4$ alkenyl group is a linear or branched alkenyl group containing from 2 to 4 carbon atoms and having one or two double bonds. Examples of $C_2$ to $C_4$ alkenyl groups include ethenyl, propenyl and butenyl. For the avoidance of doubt, where two alkenyl groups are present, the alkenyl groups may be the same or different.

As used herein, a $C_1$ to $C_4$ alkoxy group is a said $C_1$ to $C_4$ alkyl group attached to an oxygen atom. Examples of $C_1$ to $C_4$ alkoxy groups include methoxy, ethoxy, propoxy and butoxy. Typically, a $C_1$ to $C_4$ alkoxy group is a $C_1$ to $C_2$ alkoxy group, i.e. methoxy or ethoxy, typically methoxy. For the avoidance of doubt, where two alkoxy groups are present, the alkoxy groups may be the same or different.

As used herein, a $C_1$ to $C_4$ alkylene group is a bidentate moiety obtained by removing two hydrogen atoms from a $C_1$ to $C_4$ alkyl group. The two hydrogen atoms may be removed from the same carbon atom or from different carbon atoms. Typically a $C_1$ to $C_4$ alkylene group is a $C_1$ to $C_2$ alkylene group. Examples of $C_1$ to $C_4$ alkylene groups include methylene, ethylene, n-propylene, iso-propylene, n-butylene, sec-butylene and tert-butylene. A $C_1$ to $C_2$ alkyl group is methylene or ethylene, typically methylene. For the avoidance of doubt, where two alkylene groups are present, the alkylene groups may be the same or different.

An alkyl, alkenyl or alkoxy group may be substituted or unsubstituted. Where an alkyl, alkenyl or alkoxy group is substituted, it typically carry from one to three, e.g. one, or two, e.g. one, unsubstituted substituent selected from halogen, OH, —$NR^4R^5$ and $C_1$ to $C_4$ alkoxy, wherein $R^4$ and $R^5$ are the same or different and represent hydrogen or $C_1$ to $C_4$ alkyl, preferably hydrogen, methyl or ethyl, most preferably hydrogen. Preferred substituents are halogen, OH, methoxy, ethoxy, —$NH_2$, —$N(Me)_2$ and —$N(Et)_2$, in particular halogen, OH, methoxy or ethoxy, most preferably halogen. Where two or more substituents are present, the substituents may be the same or different.

As used herein, a halogen is typically chlorine, fluorine, bromine or iodine. In one aspect, halogen is typically chlorine, bromine or iodine. In another aspect, halogen is typically chlorine or fluorine.

As used herein, a 5- to 6-membered carbocyclic group is a saturated, unsaturated or partially unsaturated, cyclic hydrocarbon containing 5 or 6 carbon atoms. Typically, a carbocyclic group is saturated.

A saturated 5- to 6-membered carbocyclic group is cyclopentyl or cyclohexyl, typically cyclohexyl. An unsaturated 5- to 6-membered carbocyclic group is typically phenyl. A partially unsaturated 5- to 6-membered carbocyclic group is a non-aromatic cyclic hydrocarbon containing 5 or 6 carbon atoms and containing 1 or 2, e.g. 1 double bond. Examples of 5- to 6-membered partially unsaturated carbocyclic groups include cyclopentenyl, cyclopentadienyl, cyclohexenyl and cyclohexadienyl groups, preferably cyclohexenyl and cyclohexadienyl.

As used herein, a 5- to 10-membered heterocyclic group is typically a 5- or 6-membered monocyclic heterocyclic group or an 8- to 10-membered bicyclic heterocyclic group. As used herein a 5- or 6-membered monocyclic heterocyclic group is a cyclic moiety containing 5 or 6, typically 6, atoms selected from C, O, N and S in the ring, and containing at least one heteroatom, and typically one or two heteroatoms. The heteroatom or heteroatoms are typically selected from O, N, and S. A heterocyclic group may be saturated and thus contain 0 double bonds, or may be unsaturated, i.e. may contain 1, 2 or 3 double bonds. Unless otherwise stated, a 5- or 6-membered heterocyclic group as used herein may be any saturated or partially unsaturated heterocyclic group as defined herein or a 5- or 6-membered heteroaryl group as defined herein.

Examples of 5-membered saturated heterocyclic groups comprising one heteroatom include thiolanyl, tetrahydrofuranyl and pyrrolidinyl. Examples of 5-membered saturated heterocyclic groups comprising two heteroatoms include imidazolidinyl, pyrazolidinyl, oxazolidinyl, isoxazolidinyl, thiazolidinyl, isothiazolidinyl, 1,2-dioxolanyl, 1,3-dioxolanyl, 1,2-dithiolanyl, and 1,3-dithiolanyl. Examples of 6-membered saturated heterocyclic groups comprising one heteroatom include piperidinyl, oxanyl and thianyl. Examples of 6-membered saturated heterocyclic groups comprising two heteroatoms include piperazinyl, morpholinyl, thiomorpholinyl, dioxanyl, and dithianyl.

Examples of 5-membered partially unsaturated heterocyclic groups comprising one heteroatom include dihydropyrrolyl, dihydrofuranyl and dihydrothiophenyl. Examples of 5-membered partially unsaturated heterocyclic groups comprising two heteroatoms include dihydroimidazolyl, dihydropyrazolyl, dihydrooxazolyl, dihydroisoxazolyl, dihydrothiazolyl and dihydroisothiazolyl. Examples of 6-membered partially unsaturated heterocyclic groups comprising one heteroatom include dihydropyridinyl, dihydropyranyl and dihydrothiopyranyl. Examples of 6-membered partially unsaturated heterocyclic groups comprising two heteroatoms include dihydrodiazinyl, dihydrooxazinyl, dihydrothiazinyl, dihydrodioxinyl, and dihydrodithiinyl.

A 5- or 6-membered heterocyclic group is typically a saturated a 5- or 6-membered heterocyclic group. Typical examples include tetrahydrofuranyl, pyrrolidinyl, piperidinyl, piperazinyl, morpholinyl and thiomorpholinyl, e.g. piperidinyl, piperazinyl and morpholinyl, in particular piperazinyl.

Examples of 8- to 10-membered heterocyclic rings include indolyl, isoindolyl, benzimidazolyl, indazolyl, benzothiophenyl, dihydrothiophenyl, tetrahydrothiophenyl, benzofuranyl, dihydrobenzofuranyl and tetrahydrobenzofuranyl.

As used herein a 5- to 10-membered heteroaryl group is a cyclic, aromatic group containing from 5- to 10-atoms selected from C, O, N and S in the ring, and containing at least one heteroatom, and typically one or two heteroatoms. The heteroatom or heteroatoms, which may be the same or different, are typically selected from O, N, and S. A 5- to 10-membered heteroaryl group is typically a 5- or 6-membered monocyclic heteroaryl group or an 8- to 10-membered bicyclic heteroaryl group. Typically, a 5- to 10-membered heteroaryl group is a 5- or 6-membered monocyclic heteroaryl group, e.g. a 6-membered heteroaryl group.

Examples of 5-membered heteroaryl groups comprising one heteroatom include pyrrolyl, furanyl and thiophenyl. Examples of 5-membered heteroaryl groups comprising two heteroatoms include imidazolyl, pyrazolyl, oxazolyl, thiazolyl, isoxazolyl and isothiazolyl. Examples of 6-membered heteroaryl groups comprising one heteroatom include pyridinyl, pyranyl and thiopyranyl. Examples of 6-membered heteroaryl groups comprising two heteroatoms include diazinyl, oxazinyl, thiazinyl, dioxinyl, and dithiinyl. Typically, a 5- or 6-membered heteroaryl group is a pyrrolyl, furanyl, thiophenyl or pyridinyl group, e.g. a pyridinyl group.

Examples of 8- to 10-membered bicyclic heteroaryl groups include benzofuranyl, isobenzofuranyl, benzothiophenyl, indolyl, indazolyl, purinyl, cinnolinyl, quinoxalinyl, naphthyridinyl, naphthyridinyl, benzimidazolyl, benzoxazolyl, quinolinyl, quinazolinyl and isoquinolinyl. Typical examples are benzothiophenyl, indolyl and isoindolyl.

As used herein, a $C_6$ to $C_{10}$ aryl group is a monocyclic or fused polycyclic aromatic group. Examples include phenyl (i.e. monocyclic), naphthyl, indenyl and indanyl (i.e. fused bicyclic) groups, typically phenyl or naphthyl, most preferably phenyl.

An aryl, heteroaryl, carbocyclic or heterocyclic group as used herein may be unsubstituted or substituted with 1, 2, 3 or 4, typically 1, 2 or 3, e.g. 1 or 2 substituents. The substituents are typically selected from halogen, OH, —$NR^4R^5$, CN, $NO_2$, —$C(O)R^4$, —$C(O)OR^4$, —$C(O)NR^4R^5$, —$S(O)R^4$, and from $C_1$ to $C_4$ alkyl, $C_1$ to $C_4$ alkoxy and $C_2$ to $C_4$ alkenyl groups which are themselves unsubstituted or substituted with from 1 to 3 further unsusbtituted substituents selected from halogen, OH, —$NR^4R^5$ and $C_1$ to $C_4$ alkoxy. In one aspect, the substituents are selected from halogen, OH, $NO_2$, —$NR^4R^5$, —$C(O)OR^4$ and from $C_1$ to $C_4$ alkyl, $C_1$ to $C_4$ alkoxy and $C_2$ to $C_4$ alkenyl groups which are themselves unsubstituted or substituted with from 1 to 3 further unsubstituted substituents selected from halogen, OH, —$NR^4R^5$ and $C_1$ to $C_4$ alkoxy.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aralkyl amines and heterocyclic amines. The compounds described herein may comprise a carboxylic acid group and/or a thiol group. Typical pharmaceutically acceptable salts of such compounds comprise a salt of the carboxylic acid and/or thiol with a pharmaceutically acceptable base.

In Formula (I), the stereochemistry is not limited. In particular, compounds of formula (I) containing one or more chiral centre may be used in enantiomerically or diastereoisomerically pure form, or in the form of a mixture of isomers. Further, cis- and trans-isomers around the double bond of the thioenolate, and mixtures thereof, are envisaged. Typically, the compound described herein contains at least 50%, preferably at least 60, 75%, 90% or 95% of a compound according to Formula (I) which is isomerically pure. Thus, the compound is preferably a substantially pure isomer.

Further, for the avoidance of doubt, the compounds of the invention may be used in any tautomeric form. Thus, whilst the compounds are depicted in the form of the thioenolate, which is believed to be the predominant form, the compounds may be in the form of the corresponding mercapto compound:

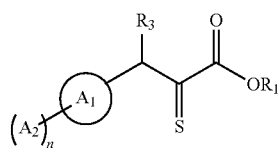

Typically, in the compounds described herein, $R^1$ is hydrogen, methyl or ethyl, preferably hydrogen.

Typically, $R^3$ is hydrogen, halogen, methyl, ethyl, OH, methoxy or ethoxy. Preferably, $R^3$ is hydrogen.

Ring A1 is typically phenyl or a 5- to 10-membered heteroaryl group containing one heteroatom selected from N, O and S. Preferred rings A1 are phenyl, furanyl, thiophenyl, pyrrolyl, pyridyl, indolyl, isoindolyl, benzofuranyl and benzothiophenyl, in particular phenyl.

The aryl or heteroaryl ring A1 is typically unsubstituted or substituted with from 1 to 4 substituents, e.g. 1, 2 or 3 substituents, in addition to the optional presence of group A2.

Two or three substituents on A1 are preferred. The substituents are typically unsubstituted substituents selected from halogen, OH, $NO_2$, —$NR^4R^5$, —$CF_3$, —$C(O)R^4$, —$C(O)OR^4$, —$C(O)NR^4R^5$, —$S(O)R^4$, $C_1$ to $C_4$ alkyl, $C_1$ to $C_4$ alkoxy and $C_2$ to $C_4$ alkenyl, wherein $R^4$ and $R^5$ independently represent hydrogen or $C_1$-$C_2$ alkyl. Preferred substituents are halogen, e.g. chorine, bromine or iodine, $NO_2$, methyl, methoxy, —$CO_2R^4$, —$COR^4$ and —$S(O)R^4$, wherein $R^4$ represents hydrogen or $C_1$-$C_2$ alkyl. Halogen and methyl, e.g. halogen, are most preferred. In one preferred aspect, ring A1 carries at least two substituents in the diortho positions relative to the thioenolate group. One or more further substituents are optionally present in the meta and/or para positions on the ring. The substituents in the ortho positions are typically those described above. Compounds having diortho substitution are understood to have beneficial MBL inhibition.

n may represent 0 or 1, preferably 0. When n represents 1, the ring A2 may be in the ortho, meta or para position relative to the thioenolate group on A1, preferably it is in the para position.

Ring A2 is typically phenyl or a 5- to 6-membered heteroaryl group containing one heteroatom selected from N, O and S. Preferred rings A2 are phenyl and pyridyl, in particular phenyl.

The aryl or heteroaryl ring A2 is typically unsubstituted or substituted with from 1 to 4 substituents, e.g. 1, 2 or 3 substituents, typically 1 or 2 substituents. The substituents are typically unsubstituted substituents selected from halogen, OH, $NO_2$, —$NR^4R^5$, —$CF_3$, —$C(O)R^4$, —$C(O)OR^4$, —$C(O)NR^4R^5$, —$S(O)R^4$, $C_1$ to $C_4$ alkyl, $C_1$ to $C_4$ alkoxy and $C_2$ to $C_4$ alkenyl, wherein $R^4$ and $R^5$ independently represent hydrogen or $C_1$-$C_2$ alkyl. Preferred substituents are halogen, e.g. fluorine or chlorine, OH, —$NH_2$, methyl or methoxy. Typically A2 is unsubstituted.

Each $R^4$ and $R^5$ in the formula (I) may be the same or different. Each typically independently represents hydrogen, methyl or ethyl, preferably hydrogen.

In one aspect of the invention, in the compounds of formula (I):
$R^1$ is hydrogen, methyl or ethyl;
$R^3$ is hydrogen, halogen, methyl, ethyl, OH, methoxy or ethoxy;
Ring A1 is phenyl or a 5- to 10-membered heteroaryl group containing one heteroatom selected from N, O and S, wherein the aryl or heteroaryl ring A1 is unsubstituted or substituted with from 1 to 4 unsubstituted substituents selected from halogen, OH, $NO_2$, —$NR^4R^5$, —$CF_3$, —$C(O)R^4$, —$C(O)OR^4$, —$C(O)NR^4R^5$, —$S(O)R^4$, $C_1$ to $C_4$ alkyl, $C_1$ to $C_4$ alkoxy and $C_2$ to $C_4$ alkenyl;
n is 0 or 1;
Ring A2 is phenyl or a 5- to 6-membered heteroaryl group containing one heteroatom selected from N, O and S, wherein the aryl or heteroaryl ring A2 is unsubstituted or substituted with from 1 to 4 unsubstituted substituents selected from halogen, OH, $NO_2$, —$NR^4R^5$, —$CF_3$, —$C(O)R^4$, —$C(O)OR^4$, —$C(O)NR^4R^5$, —$S(O)R^4$, $C_1$ to $C_4$ alkyl, $C_1$ to $C_4$ alkoxy and $C_2$ to $C_4$ alkenyl; and
$R^4$ and $R^5$ each independently represent hydrogen, methyl or ethyl.

In a preferred aspect of the invention, the compounds described herein are thioenolates of formula (IA) or pharmaceutically acceptable salts thereof:

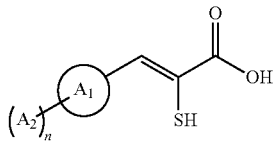

Formula (IA)

wherein

Ring A1 is phenyl, furanyl, thiophenyl, pyrrolyl, pyridyl, indolyl, isoindolyl, benzofuranyl or benzothiophenyl, A1 being unsubstituted or substituted with 1, 2 or 3 substituents selected from halogen, e.g. chorine, bromine or iodine, $NO_2$, methyl, methoxy, —$CO_2R^4$, —$COR^4$, and —$S(O)R^4$, wherein $R^4$ represents hydrogen or $C_1$-$C_2$ alkyl;

n is 0 or 1;

Ring A2 is phenyl or pyridyl, A2 being unsubstituted or substituted with 1, 2 or 3 unsubstituted substituents selected from halogen, e.g. fluorine or chlorine, OH, —$NH_2$, methyl or methoxy, wherein A2 is preferably unsubstituted.

In a preferred aspect, in formula (IA), ring A1 is a phenyl ring.

Preferably, in the above embodiment, ring A1 carries at least two substituents in the diortho positions relative to the thioenolate group. The substituents are preferably halogen atoms.

Examples of compounds of the invention include (Z)-2-mercapto-3-(2,3,6-trichlorophenyl)acrylic acid and pharmaceutically acceptable salts thereof, and esters of (Z)-2-mercapto-3-(2,3,6-trichlorophenyl)acrylic acid including methyl (Z)-2-mercapto-3-(2,3,6-trichlorophenyl)acrylate and ethyl (Z)-2-mercapto-3-(2,3,6-trichlorophenyl)acrylate, as well as pharmaceutically acceptable salts of these esters.

Further examples of compounds of the invention include:
(Z)-2-mercapto-3-(2,3,6-triiodophenyl)acrylic acid
(Z)-2-mercapto-3-(2,3,6-tris(methylsulfinyl)phenyl)acrylic acid;
(Z)-3-([1,1'-biphenyl]-4-yl)-2-mercaptoacrylic acid;
(Z)-2-mercapto-3-phenylacrylic acid;
(Z)-2-mercapto-3-(p-tolyl)acrylic acid;
(Z)-2-mercapto-3-(4-methoxyphenyl)acrylic acid;
(Z)-2-mercapto-3-(4-(methoxycarbonyl)phenyl)acrylic acid;
(Z)-3-(4-fluorophenyl)-2-mercaptoacrylic acid;
(Z)-3-(4-chlorophenyl)-2-mercaptoacrylic acid;
(Z)-3-(4-bromophenyl)-2-mercaptoacrylic acid;
(Z)-3-(furan-2-yl)-2-mercaptoacrylic acid;
(Z)-2-mercapto-3-(1-methyl-1H-pyrrol-2-yl)acrylic acid; and
(Z)-3-(4-formylphenyl)-2-mercaptoacrylic acid.

As well as esters (e.g. methyl or ethyl esters) of the above compounds and pharmaceutically acceptable salts of the acids and of the esters. The 2,3,6-substituted compounds are preferred.

(E)-isomers of the above compounds, or mixtures of (E) and (Z) forms may also be provided.

Certain novel compounds are also provided. These compounds are thioenolates of formula (I) or pharmaceutically acceptable salts thereof:

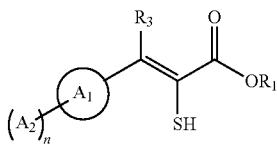

Formula (I)

wherein $R^1$ is H or a $C_1$ to $C_4$ alkyl group;

$R^3$ is H, halogen, $C_1$ to $C_4$ alkyl, OH, $C_1$ to $C_4$ alkoxy, $C_2$ to $C_4$ alkenyl, or —$NR^4R^5$;

Ring A1 is a $C_6$ to $C_{10}$ aryl or 5- to 10-membered heteroaryl group which is unsubstituted or substituted with 2, 3 or 4 substituents, wherein two of the substituents are in the diortho positions relative to the thioenolate group, and wherein the substitutents are selected from halogen, OH, —$NR^4R^5$, CN, $NO_2$, —$C(O)R^4$, —$C(O)OR^4$, —$C(O)NR^4R^5$, —$S(O)R^4$, and from $C_1$ to $C_4$ alkyl, and $C_2$ to $C_4$ alkenyl groups which are themselves unsubstituted or substituted with from 1 to 3 further unsubstituted substituents selected from halogen, OH, —$NR^4R^5$ and $C_1$ to $C_4$ alkoxy;

n is 0 or 1;

Ring A2 is a $C_6$ to $C_{10}$ aryl or 5- to 10-membered heteroaryl group which is unsubstituted or substituted with from 1 to 4 substituents selected from halogen, OH, —$NR^4R^5$, CN, $NO_2$, —$C(O)R^4$, —$C(O)OR^4$, —$C(O)NR^4R^5$, —$S(O)R^4$, and from $C_1$ to $C_4$ alkyl, $C_1$ to $C_4$ alkoxy and $C_2$ to $C_4$ alkenyl groups which are themselves unsubstituted or substituted with from 1 to 3 further unsubstituted substituents selected from halogen, OH, —$NR^4R^5$ and $C_1$ to $C_4$ alkoxy; and $R^4$ and $R^5$ each independently represent H or $C_1$ to $C_4$ alkyl.

$R^1$, $R^3$, $R^4$, $R^5$ and A1 and A2 are preferably as described herein, with the proviso that A1 carries at least two substituents in the diortho positions relative to the thioenolate group, and the substituents on A1 are not alkoxy groups.

In one aspect, the thioenolate of formula (I) or pharmaceutically acceptable salt thereof may be used in combination with a rhodanine. The present invention therefore provides combinations of the thioenolate of formula (I) or pharmaceutically acceptable salt thereof with a compound which is a rhodanine of formula (II) or a pharmaceutically acceptable salt thereof:

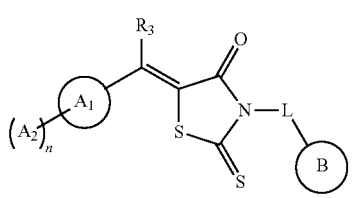

Formula (II)

wherein A1, A2, n and $R^3$ are as defined herein;

L is a linker of formula -(Alk$^1$)$_p$-(Het)$_q$-(Alk$^2$)$_r$-, wherein Alk$^1$ and Alk$^2$ independently represent $C_1$ to $C_4$ alkylene and Het represents —O—, —S—, —$NR^4$—, —C(O)—, —C(O)O— or —C(O)$NR^4$—, and p, q and r are each independently 0 or 1;

Ring B is a 5- to 6-membered carbocyclic or 5- to 10-membered heterocyclic group, which is unsubstituted or substituted with 1, 2 or 3 substituents selected from halogen, OH, $NO_2$, —$NR^4R^5$, —$C(O)OR^4$ and from $C_1$ to $C_4$ alkyl, $C_1$ to $C_4$ alkoxy and $C_2$ to $C_4$ alkenyl groups which are themselves unsubstituted or substituted with from 1 to 3 further unsubstituted substituents selected from halogen, OH, —$NR^4R^5$ and $C_1$ to $C_4$ alkoxy; and $R^4$ and $R^5$ each independently represent H or $C_1$ to $C_4$ alkyl.

Typically, L is a linker of formula -$(Alk^1)_p$-$(Het)_q$-$(Alk^2)_r$-, wherein $Alk^1$ and $Alk^2$ independently represent methylene or ethylene, Het represents —O—, —S—, —$NR^4$—, —C(O)—, —C(O)O— or —C(O)$NR^4$—, $R^4$ represents hydrogen, methyl or ethyl, and p, q and r are each independently 0 or 1. Preferably, L is a linker of formula —$(CH_2)_p$-$(Het)_q$-$(CH_2)_r$—, wherein Het represents —O—, —NH—, —C(O)—, —C(O)O— or —C(O)NH—, and p, q and r are each independently 0 or 1. Preferably q is 1 and p and r each independently 0 or 1. For example p may be 1, q may be 1 and r may be 0 or 1, e.g. 0. A particularly preferred linker is —$CH_2$—CO—NH—.

Typically ring B is a 5- to 6-membered carbocyclic, 5- to 6-membered monocyclic heterocyclic or 8- to 10-membered bicyclic heterocyclic group, preferably a 5- to 6-membered carbocyclic or 5- to 6-membered monocyclic heterocyclic group. Examples of ring B include phenyl, cyclohexyl and 5- to 6-membered heterocyclic groups, for example phenyl, cyclohexyl, pyridyl, tetrahydrofuranyl, piperidinyl, piperazinyl, morpholinyl, imidazolyl, oxazolyl and isoxazolyl. Typically B is a 5- to 6-membered, saturated carbocyclic or heterocyclic group. Preferred groups B include cyclohexyl, piperidinyl, piperazinyl and morpholinyl, in particular piperazinyl.

B is unsubstituted or substituted with 1, 2 or 3 substituents, for example 1 or 2, e.g. 1, substituent. The substituents are typically selected from the unsubstituted substituents halogen, OH, —$NR^4R^5$, $C_1$ to $C_4$ alkyl, $C_1$ to $C_4$ alkoxy and $C_2$ to $C_4$ alkenyl, wherein $R^4$ and $R^5$ each independently represent H or $C_1$ to $C_2$ alkyl. Preferred substituents include halogen, e.g. fluorine and chlorine, OH, —$NH_2$, methyl and methoxy, in particular methyl.

In one aspect of the invention, in formula (II):
$R^3$ is hydrogen, halogen, methyl, ethyl, OH, methoxy or ethoxy;
Ring A1 is phenyl or a 5- to 10-membered heteroaryl group containing one heteroatom selected from N, O and S, wherein the aryl or heteroaryl ring A1 is unsubstituted or substituted with from 1 to 4 unsubstituted substituents selected from halogen, OH, $NO_2$, —$NR^4R^5$, —$CF_3$, —C(O)$R^4$, —C(O)O$R^4$, —C(O)$NR^4R^5$, —S(O)$R^4$, $C_1$ to $C_4$ alkyl, $C_1$ to $C_4$ alkoxy and $C_2$ to $C_4$ alkenyl;
n is 0 or 1;
Ring A2 is phenyl or a 5- to 6-membered heteroaryl group containing one heteroatom selected from N, O and S, wherein the aryl or heteroaryl ring A2 is unsubstituted or substituted with from 1 to 4 unsubstituted substituents selected from halogen, OH, $NO_2$, —$NR^4R^5$, —$CF_3$, —C(O)$R^4$, —C(O)O$R^4$, —C(O)$NR^4R^5$, —S(O)$R^4$, $C_1$ to $C_4$ alkyl, $C_1$ to $C_4$ alkoxy and $C_2$ to $C_4$ alkenyl;
L is a linker of formula -$(Alk^1)_p$-$(Het)_q$-$(Alk^2)_r$-, wherein $Alk^1$ and $Alk^2$ independently represent methylene or ethylene, Het represents —O—, —S—, —$NR^4$—, —C(O)—, —C(O)O— or —C(O)$NR^4$—, and p, q and r are each independently 0 or 1;
Ring B is phenyl, cyclohexyl or a 5- to 6-membered heterocyclic group which is unsubstituted or substituted with 1, 2 or 3 unsubstituted substituents selected from halogen, OH, —$NR^4R^5$, $C_1$ to $C_4$ alkyl, $C_1$ to $C_4$ alkoxy and $C_2$ to $C_4$ alkenyl; and
$R^4$ and $R^5$ each independently represent hydrogen, methyl or ethyl.

In a preferred aspect of the invention, the compounds of formula (II) are compounds of formula (IIA):

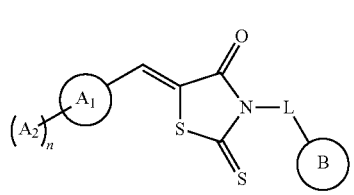

Formula (IIA)

wherein
Ring A1 is phenyl, furanyl, thiophenyl, pyrrolyl, pyridyl, indolyl, isoindolyl, benzofuranyl or benzothiophenyl, A1 being unsubstituted or substituted with 1, 2 or 3 substituents selected from halogen, e.g. chorine, bromine or iodine, $NO_2$, methyl, methoxy, —$CO_2R^4$, —$COR^4$, and —$S(O)R^4$, wherein $R^4$ represents hydrogen or $C_1$-$C_2$ alkyl;
n is 0 or 1;
Ring A2 is phenyl or pyridyl, A2 being unsubstituted or substituted with 1, 2 or 3 unsubstituted substituents selected from halogen, e.g. fluorine or chlorine, OH, —$NH_2$, methyl or methoxy, wherein A2 is preferably unsubstituted;
L is a linker of formula —$(CH_2)_p$-(Het)-$(CH_2)_r$—, wherein Het represents —O—, —NH—, —C(O)—, —C(O)O— or —C(O)NH—, and p and r are each independently 0 or 1; preferably L is —$CH_2$—CO—NH—; and
B is cyclohexyl, pyridinyl, pyrazinyl and morpholinyl, preferably pyrazinyl, wherein B is unsubstituted or substituted with 1 or 2 unsubstituted substituents selected from halogen, e.g. fluorine and chlorine, OH, —$NH_2$, methyl and methoxy.

Preferably, in the above embodiment, ring A1 carries at least two substituents in the diortho positions relative to the thioenolate group. The substituents are preferably halogen atoms.

Preferred examples of a compound of formula (II) are (Z)—N-(4-methylpiperazin-1-yl)-2-(4-oxo-2-thioxo-5-(2,3,6-trichlorobenzylidene)thiazolidin-3-yl)acetamide and pharmaceutically acceptable salts thereof.

The rhodanines of formula (II) having a linker L of formula -$(Alk)_p$-(CONH)-$(Alk)_r$- can be obtained in accordance with Scheme 1 below, by (1) attachment of ring(s) A1-$(A2)_n$ to the rhodanine precursor compound (III), and (2) attachment of the moiety -L-B. Where the Het group is other than an amide group, corresponding synthetic techniques known to the skilled chemist can be used to connect the -L-B group. Synthetic routes are also described by Spicer et al in Probe Reports from the NIH Molecular Libraries Program. Beth Seda (MD): National Center for Biotechnology Information (US); 2010. The thioenolates of formula (I) can be obtained by hydrolysis of the rhodanines of formula (II), for example hydrolysis under basic conditions.

Scheme 1

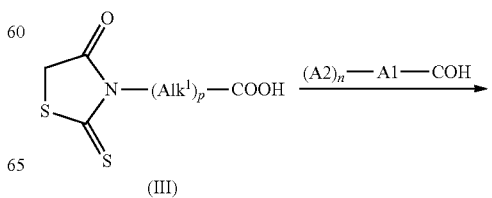

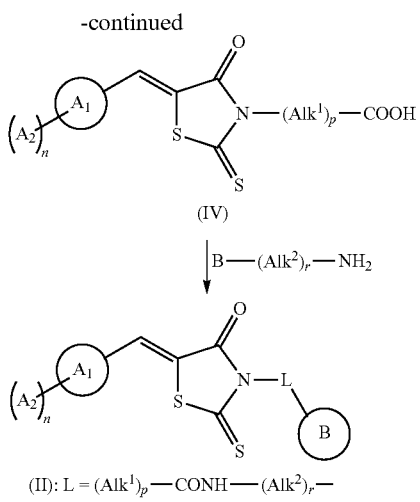

In the following description, unless otherwise stated, reference to thioenolates indicates the compounds which are thioenolates of formula (I) and pharmaceutically acceptable salts thereof. Further, reference to rhodanines indicates the compounds which are rhodanines of formula (II) and pharmaceutically acceptable salts thereof.

In one aspect, where the thioenolate and rhodanine are used in combination, A1, A2, n and $R^3$ are the same in formulae (I) and (II). The thienolate and rhodanine may be provided as a single formulation containing both active ingredients. Alternatively, they may be provided in separate formulations. The separate formulations may be administered simultaneously or separately.

The thioenolates and combinations described herein are therapeutically useful. The present invention therefore provides thioenolates and combinations as described herein, for use in treating the human or animal body. Also provided is a pharmaceutical composition comprising a thioenolate or combination as described herein together with a pharmaceutically acceptable carrier or diluent. Typically, the composition contains up to 85 wt %, e.g. up to 50 wt % of active agent, for example up to 85 wt %, e.g. up to 50 wt % of a thioenolate. In the case of a combination, the combination of thioenolate and rhodanine typically forms up to 85 wt %, e.g. up to 50 wt % of the composition. Preferred pharmaceutical compositions are sterile and pyrogen free. Further, the pharmaceutical compositions provided by the invention typically contain a thioenolate and/or a rhodanine which is a substantially pure isomer.

In one aspect, the composition of the invention also comprises a β lactam antibiotic agent. Thus, the composition comprises a pharmaceutically acceptable carrier or diluent and:
(i) a compound which is a thioenolate of formula (I) or a pharmaceutically acceptable salt thereof; and optionally one or both of
(ii) a compound which is a rhodanine of formula (II) or a pharmaceutically acceptable salt thereof; and
(iii) a β lactam antibiotic agent.

Where the β lactam antibiotic agent is provided in the same composition, typically the total combined weight of thioenolate, rhodanine (if present) and β lactam antibiotic agent is up to 85 wt %, typically up to 50 wt %.

Therapeutic Uses

The thioenolates and combinations described herein are useful in the inhibition of MBLs. Many bacteria have developed resistance to β-lactam antibiotic agents, one of the resistance mechanisms being the hydrolysis of the β-lactam by MBLs. The inhibition of bacterial MBLs by the compounds and combinations described herein therefore significantly enhances the activity of β-lactam antibiotic agents. Thus, on administration to a subject, the thioenolates and combinations described herein may inhibit the MBL-catalysed resistance of bacteria to β-lactam antibiotic agents. The thioenolates and combinations are therefore useful in the potentiation of the activity of β-lactam antibiotic agents. They are also useful in the prevention or treatment of bacterial infection when used in combination with a β-lactam antibiotic agent. Accordingly, the present invention provides (i) a compound which is a thioenolate of formula (I) or a pharmaceutically acceptable salt thereof, or (ii) a combination as described herein, for use in a method of inhibiting bacterial metallo-beta-lactamase (MBL). Also provided is a method of inhibiting bacterial metallo-beta-lactamase (MBL) activity in a subject, which method comprises administration to the subject of an effective amount of (i) a compound which is a thioenolate of formula (I) or a pharmaceutically acceptable salt thereof or (ii) a combination as described herein. Also provided is (i) a compound which is a thioenolate of formula (I) or a pharmaceutically acceptable salt thereof, or (ii) a combination as described herein, for use in the manufacture of a medicament for use in a method of inhibiting bacterial metallo-beta-lactamase (MBL). The method described herein may be a method of potentiating the activity of a β-lactam antibiotic agent.

Also provided is (i) a compound which is a thioenolate of formula (I) or a pharmaceutically acceptable salt thereof or (ii) a combination as described herein, for use in combination with a β-lactam antibiotic agent in the prevention or treatment of bacterial infection. Also provided is a method for the prevention or treatment of bacterial infection in a subject, which method comprises administering to said subject a β-lactam antibiotic agent and either (i) a compound which is a thioenolate of formula (I) or a pharmaceutically acceptable salt thereof or (ii) a combination as described herein. Also provided is the use of (i) a compound which is a thioenolate of formula (I) or a pharmaceutically acceptable salt thereof or (ii) a combination as described herein in the manufacture of a medicament for use in the prevention or treatment of bacterial infection in combination with a β-lactam antibiotic agent.

Also provided herein is an antibiotic combination comprising the compound or combination described herein and a β-lactam antibiotic agent. The β-lactam antibiotic agent and the thioenolate or combination described herein may be provided in a single formulation. Alternatively, the β-lactam antibiotic agent may be provided in a separate formulation. Where administered together with the combination described herein, the β-lactam antibiotic agent may be formulated together with none, one or both of the active agents of the combination (namely the thioenolate and the rhodanine).

The β-lactam antibiotic agent, thioenolate and, where used, the rhodanine may be administered simultaneously or separately from one another. Where all three active agents are used, all three may be administered simultaneously, two may be administered simultaneously and the third separately (for example the thioenolate and rhodanine may be administered simultaneously and the antibiotic agent separately) or all three agents may be administered separately from one another.

The present invention also provides a kit comprising:
(i) a compound which is a thioenolate of formula (I) or a pharmaceutically acceptable salt thereof; and one or both of
(ii) a compound which is a rhodanine of formula (II) or a pharmaceutically acceptable salt thereof; and/or
(iii) a β-lactam antibiotic agent.

The kit may further comprise instructions for the administration of the thioenolate in combination with one or both of the rhodanine and the β-lactam antibiotic agent.

In the antibiotic combination of the present invention and the kit of the present invention the ratio of β-lactam antibiotic agent to the compound of formula (I) is typically from 20:1 to 1:20, for example from 10:1 to 1:20, preferably from 1:1 to 1:10, more preferably from 1:3 to 1:9, e.g. about 1:4 or about 1:8, from 1:3.5 to 1:4.5, or from 1:7.5 to 1:8.5. In some embodiments of the antibiotic combination of the present invention and the kit of the present invention, the compound of formula (I) and the β-lactam antibiotic agent are present in a synergistic combination.

The β-lactam antibiotic agent may be any antibiotic agent which comprises a β-lactam and is therefore susceptible to degradation by β-lactamases. Examples include carbapenems (e.g. meropenem, faropenem, imipenem, ertapenem, doripenem, panipenem/betamipron and biapenem as well as razupenem, tebipenem, lenapenem and tomopenem), ureidopenicillins (e.g. piperacillin), carbacephems (e.g. loracarbef) and cephalosporins (e.g. cefpodoxime, ceftazidime, cefotaxime, ceftriaxone, ceftobiprole, and ceftaroline). Specific examples of β-lactam antibiotic agents include temocillin, piperacillin, cefpodoxime, ceftazidime, cefotaxime, ceftriaxone, meropenem, faropenem, imipenem, loracarbef, ceftobiprole, ceftaroline.

The bacterial infection may be caused by Gram-negative or Gram-positive bacteria. For example, the bacterial infection may be caused by bacteria from one or more of the families *Clostridium, Pseudomonas, Escherichia, Klebsiella, Enterococcus, Enterobacter, Serratia, Morganella, Yersinia, Salmonella, Proteus, Pasteurella, Haemophilus, Citrobacter, Burkholderia, Brucella, Moraxella, Mycobacterium, Streptococcus* or *Staphylococcus*. Particular examples include *Clostridium, Pseudomonas, Escherichia, Klebsiella, Enterococcus, Enterobacter, Streptococcus* and *Staphylococcus*. The bacterial infection may, for example, be caused by one or more bacteria selected from *Moraxella catarrhalis, Brucella abortus, Burkholderia cepacia, Citrobacter species, Escherichia coli, Haemophilus* Pneumonia, *Klebsiella Pneumonia, Pasteurella multocida, Proteus mirabilis, Salmonella typhimurium, Clostridium difficile, Yersinia enterocolitica Mycobacterium tuberculosis, Staphylococcus aureus*, group B streptococci, *Streptococcus Pneumonia*, and *Streptococcus pyogenes* e.g. from *E. coli* and *K. pneumoniae*.

A compound or combination of the invention can be administered to the subject in order to prevent the onset of one or more symptoms of the bacterial infection. This is prophylaxis. In this embodiment, the subject can be asymptomatic. The subject is typically one that has been exposed to the bacterium. A prophylactically effective amount of the agent or formulation is administered to such a subject. A prophylactically effective amount is an amount which prevents the onset of one or more symptoms of the bacterial infection.

A compound or combination of the invention can be administered to the subject in order to treat one or more symptoms of the bacterial infection. In this embodiment, the subject is typically symptomatic. A therapeutically effective amount of the compound or combination is administered to such a subject. A therapeutically effective amount is an amount effective to ameliorate one or more symptoms of the disorder.

In one aspect the subject is a mammal, in particular a human. However, the subject may be a non-human animal, including but not limited to primates such as monkeys, commercially farmed animals such as horses, cows, sheep or pigs and domestic pets such as dogs, cats, guinea pigs, rabbits, hamsters or gerbils. The subject can be any animal that is capable of being infected by a bacterium.

The compound or combination of the invention may be administered in a variety of dosage forms. Thus, it can be administered orally, for example as tablets, troches, lozenges, aqueous or oily suspensions, dispersible powders or granules. The compound or combination of the invention may also be administered parenterally, whether subcutaneously, intravenously, intramuscularly, intrasternally, transdermally or by infusion techniques. The compound or combination may also be administered as a suppository or via inhaled (aerosolised) administration. Oral or parenteral, e.g. oral, administration is preferred.

The compound or combination of the invention is typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions. Pharmaceutical compositions suitable for delivery by needleless injection, for example, transdermally, may also be used.

A therapeutically or prophylactically effective amount of the compound or combination of the invention is administered to a subject. The close may be determined according to various parameters, especially according to the compound used; the age, weight and condition of the subject to be treated; the route of administration; and the required regimen. Again, a physician will be able to determine the required route of administration and dosage for any particular subject. A typical daily dose is from about 0.01 to 100 mg per kg, preferably from about 0.1 mg/kg to 50 mg/kg, e.g.

from about 1 to 10 mg/kg of body weight, according to the activity of the specific inhibitor, the age, weight and conditions of the subject to be treated, the type and severity of the disease and the frequency and route of administration. Preferably, daily dosage levels are from 5 mg to 2 g.

Diagnostic Uses

The antibiotic combinations described herein, comprising the compound or combination described herein and a β-lactam antibiotic agent, can also be used in methods for the detection of metallo-beta-lactamases. Thus, a sample containing bacteria which is suspected of expressing metallo-beta-lactamases can be cultured (a) in the presence of a beta-lactam antibiotic agent; and (b) in the presence of the antibiotic combination of the invention. If the bacteria are seen to grow under conditions (a), this suggests that a beta-lactamase, able to hydrolyse the antibiotic agent, is causing resistance of the bacteria to the antibiotic agent. However, if the bacteria do not grow under condition (b), i.e. in the presence of a thienolate of the invention and an antibiotic agent, then the beta-lactamases present have been inhibited. Such a result suggests that the beta-lactamases are metallo-beta-lactamases. The method can be used to determine whether bacteria express metallo-beta-lactamase enzymes.

Thus, the present invention provides a method comprising culturing a sample (e.g. a urine, blood or plasma sample of a subject, or bacteria isolated from urine, blood or plasma of a subject), in particular a sample which comprises, or is suspected of comprising bacteria, in the presence of an antibiotic combination of the invention. The method may also comprise a step of culturing a further sample of the same material in the presence of the same antibiotic agent, but in the absence of the compound or combination of the invention.

The method may be used to determine an appropriate treatment for a subject suspected of having a bacterial infection, and in particular to determine whether treatment of said subject with a metallo-beta-lactamase inhibitor, in combination with a beta-lactam antibiotic agent, will be of benefit to the subject.

The methods may be carried out in accordance with the techniques described in U.S. Pat. No. 7,807,403. Thus for example, the method may comprise providing a culture of the bacteria mixed with the antibiotic combination of the invention and a permeabilizing agent for the bacteria (in an amount which does not inhibit growth but allows permeation), to form an assay culture. The assay culture may be maintained (incubated) under appropriate culture conditions and for a time period sufficient to allow the bacteria to interact with the antibiotic agent and the thioenolate.

The thioenolate may be present in an amount of about 5 to about 250 μg per standard interaction test disk and more usually about 5 to about 50 μg, or in a proportional amount if a different assay format is utilized.

The permeabilizing agent may be dissolved or dispersed in a carrier, for example an aqueous buffer solution such as Tris/EDTA (TE). The carrier can be a solid carrier, e.g. a paper disk, or a liquid carrier. A growth medium may be provided. Suitable permeabilising agents are those which may permeate the cell wall of a bacterium and examples are provided in U.S. Pat. No. 7,807,403.

EXAMPLES

Material and Methods

Chemicals were from commonly used suppliers and were used without further purification. Solvents (including dry solvents) for chemical transformations, work-up and chromatography were from Sigma-Aldrich (Dorset, UK) at HPLC grade, and used without further distillation. Silica gel 60 F254 analytical thin layer chromatography (TLC) plates were from Merck (Darmstadt, Germany) and visualized under UV light and/or with potassium permanganate stain. Chromatographic purifications were performed using Merck Geduran 60 silica (40-63 rpm) or prepacked SNAP columns using a Biotage SP1 Purification system (Uppsala, Sweden). Microwave assisted reactions were performed using a Biotage Initiator™ microwave synthesizer in sealed vials. Deuterated solvents were obtained from Chambridge Isotopes and Apollo Scientific Ltd. All $^1$H and $^{13}$C NMR spectra were recorded using a Bruker Avance 400 MHz spectrometer. All chemical shifts are given in ppm relative to the solvent peak,[14] and coupling constants (J) are reported in Hz to the closed 0.5. High Resolution (HR) mass spectrometry data (m/z) were obtained from a Bruker MicroTOF instrument using an ESI source and Time of Flight (TOF) analyzer. Low Resolution (LR) mass spectrometry data (m/z) were obtained from a Waters LCT Premier instrument using an ESI source and Time of Flight (TOF) analyzer. Melting points were obtained using a Stuart SMP-40 automatic melting point apparatus.

$^1$H NMR Experiments

Samples for ML302 hydrolysis were prepared as follows: 0.2 mM ML302 was dissolved in 50 mM Tris-$d_{11}$/HCl buffer (90% $H_2O$, 10% $D_2O$) pH 7.5. Spectra were recorded in the absence or presence of NDM-1 (1 μM).

$^1$H NMR time-courses were recorded either on Bruker AVIII 700 with $^1$H/$^{13}$C/$^{15}$N TCI cryoprobe or Bruker AVIII 600 with BB-F/$^1$H Prodigy $N_2$ cryoprobe with a typical 256 scans (AVIII 600) or 128 scans (AVIII 700) and 900 pulse lengths were of 12 μs. Data were processed with 1 Hz (AVIII 600) or 0.3 Hz (AVIII 700) Lorentzian line broadening using TopSpin 3.1 software (Bruker).

Synthesis (See also Spicer T, et al ML302: A Novel Beta-lactamase (BLA) Inhibitor in *Probe Reports for the NIH Molecular Libraries Program* (National Center for Biotechnology Information (US) (Bethsada (MD), 2010)

(Z)-2-(4-Oxo-2-thioxo-5-(2,3,6-trichlorobenzylidene) thiazolidin-3-yl)acetic acid (1)

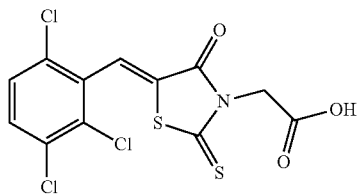 [SMILES: O=C(O)CN1C(=O)/C(=C/c2c(Cl)ccc(Cl)c2Cl)SC1=S]

A 20-mL microwave vial was charged with 2,3,6-trichlorobenzaldehdye (1.05 g, 5.0 mmol) and rhodanine-3-acetic acid (955 mg, 5.0 mmol). Ethanol (10 mL) was added followed by piperidine (4 drops). The vial was sealed and submitted to microwave irradiation at 120° C. for 90 min. The solvent was removed and the crude product purified by column chromatography ($CH_2Cl_2$/MeOH 9:1). The desired product was obtained as light yellow solid (1.35 g, 71%). TLC ($CH_2Cl_2$/MeOH 9:1) $R_f$=0.55. $^1$H NMR (400 MHz $CDCl_3$) δ=8.50-7.00 (br. s, COOH, 1H), 7.76 (s, 1H), 7.47-7.52 (m, 1H), 7.36 (d, J=9.0 Hz, 1H), 4.93 (s, 2H) ppm.

$^{13}$C NMR (101 MHz CDCl$_3$) δ=191.9, 170.9, 165.2, 132.6, 132.3, 132.2, 131.8, 131.31, 131.29, 128.7, 128.1, 44.1 ppm. LRMS m/z calcd. for C$_{12}$H$_5$Cl$_3$NO$_3$S$_2$ [M−H]=379.88, found [M−H]=379.8.

Example 1: N-(4-Methylpiperazin-1-yl)-2-(4-oxo-2-thioxo-5-(2,3,6-trichlorobenzylidene)thiazolidin-3-yl)acetamide (E/Z mixture (1:3)) (ML302)

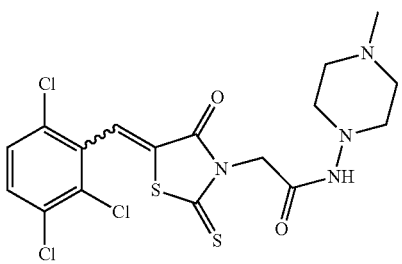 [SMILES: CN1CCN(NC(=O)CN2C(=O)C(=Cc3c(Cl)ccc(Cl)c3Cl)SC2=S)CC1]

A solution of 1 (381 mg, 1.0 mmol) and Bis(2-oxo-3-oxazolidinyl)phosphonic chloride (BOP-Cl, 350 mg, 1.2 mmol, 1.2 equiv) in CH$_2$Cl$_2$ (10 mL) was cooled to 0° C. using an ice/water bath under an inert atmosphere. Freshly distilled triethylamine (Et$_3$N, 168 μL, 1.2 mmol, 1.2 equiv) was added and the solution was allowed to stir at 0° C. for 30 min. 1-Amino-4-methyl-piperazine (145 μL, 1.2 mmol, 1.2 equiv) was added and the temperature was raised to r.t. after which the reaction was stirred overnight. The crude product, obtained by removal of dichloromethane in vacuo, was than purified by flash chromatography (CH$_2$Cl$_2$/MeOH 9:1) to give compound ML302 as a non-separated mixture of E/Z isomers in a 1:3 ratio (373 mg, 78%) as a yellow solid. TLC (CH$_2$Cl$_2$/MeOH 9:1) R$_f$=0.35. $^1$H NMR (400 MHz, CDCl$_3$) δ (assigned for the major isomer)=7.72 (s, 1H), 7.47 (dd, J=8.5, 0.5 Hz, 1H), 7.34 (d, J=9.0 Hz, 2H), 6.90 (br. s., 1H), 5.05 (s, 2H), 2.95-3.20 (m, 2H), 2.65-2.90 (m, 4H), 2.33 (s, 3H) ppm. $^{13}$C NMR (101 MHz CDCl$_3$) δ (assigned for the major isomer)=192.9, 166.9, 166.0, 133.1, 132.5, 132.08, 132.05, 128.9, 127.9, 56.0, 54.2 (4C), 45.4, 44.9 ppm. LRMS m/z calcd. for C$_{17}$H$_{18}$Cl$_3$N$_4$O$_2$S$_2$[M+H]=478.99, found [M+H]=479.0. Mp=182-185° C.

Example 2: 2-Mercapto-3-(2,3,6-trichlorophenyl) acrylic acid (E/Z mixture (1:4) (ML302F)

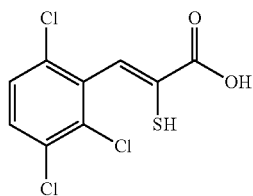 [SMILES: O=C(O)/C(S)=C/c1c(Cl)ccc(Cl)c1Cl]

Compound ML302 (240 mg, 0.5 mmol) was dissolved in 1M NaOH (4 mL) upon which a colour change to deep red was observed. The clear reaction mixture was warmed to 60° C., then stirred for 45 min (the reaction colour changes from deep red to yellow) when consumption of starting material was observed. The reaction mixture was cooled to room temperature and subsequently carefully acidified with 1M HCl (5 mL). A white precipitate was formed and collected by centrifugation (4000 g/10 min). After removal of the liquid phase the white solid was resuspended in H$_2$O (2 mL) and again collected by centrifugation. This process was repeated twice. The obtained solid was dried under high vacuum overnight. The product was obtained as an inseparable mixture of E/Z isomers in a 1:4 ratio as an off-white solid (40 mg, 28%). TLC (CH$_2$Cl$_2$/MeOH 4:1) R$_f$=0.67. $^1$H NMR (400 MHz, CDCl$_3$) δ (assigned for the major isomer) =7.69 (s, 1H), 7.45 (dd, J=8.5, 1.0 Hz, 1H), 7.33-7.37 (m, 1H), 3.89 (br. s., 1H) ppm. $^{13}$C-NMR (200 MHz, CDCl$_3$) δ=168.1, 134.7, 132.8, 132.4, 132.1, 132.1, 130.7, 130.6, 128.7 ppm. LRMS m/z calcd. for C$_9$H$_4$Cl$_3$O$_2$S [M−H] =280.90, found [M−H]=280.8.

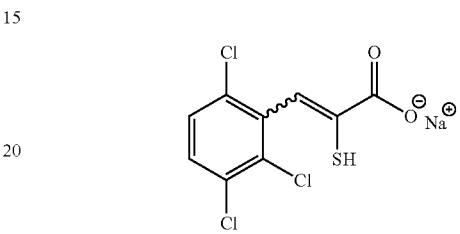

Sodium 2-mercapto-3-(2,3,6-trichlorophenyl)acrylate (ML302F-Na) was obtained by dissolving ML302F (28.2 mg, 0.1 mmol) in 0.1M NaHCO$_3$ (1 mL). The resulting clear solution was subsequently lyophilized to generate the desired sodium salt as an off-white solid (31 mg, quant). LRMS m/z calcd. for C$_9$H$_4$Cl$_3$NaO$_2$S [M+Na]=303.89, found [M−H]=280.8.

Protein Production and Purification

Recombinant forms of NDM-1, NDM-1 M67C, VIM-1, VIM-2, SPM-1, IMP-1 and BcII MBLs were produced in *Escherichia coli* as described in J. Med. Chem. 56, 6945-6953 (2013) and Makena et al Chem MechCHem 8, 1923-9 (2013). Purified VIM-2 protein was dialysed into fresh crystallization buffer (50 mM HEPES pH 7.5, 150 mM NaCl and 1 μg ZnCl$_2$, concentrated to 7.5 mg/mL and used for crystallographic analyses.

Kinetic Analyses

Kinetic and inhibition analyses and UV-VIS studies[16] against bacterial MBLs were performed as described by Van Berkel et al in J. Med. Chem. 56, 6945-6953 (2013) and Makena et al Chem MechCHem 8, 1923-9 (2013).

Example 3: Screening Assay

Screening assays to determine kinetic data and IC$_{50}$ values for ML302F, ML302 and a mixture of ML302 and ML302F (herein ML302M) were carried out as described by van Berkel, S. S. et al in J Med. Chem. 56, 6945-6953 (2013). The experiments were performed by using a NovaStar microplate reader (using path length correction) and were performed at r.t. (24-25° C.). All enzymes and substrates were dissolved in the assay buffer: 50 mM HEPES-NaOH buffer (pH 7.2) supplemented with 1 μg/mL BSA (to minimize the denaturation of the enzyme), 1 μM ZnSO$_4$ and 0.01% Triton 100. Screening was carried out against a panel of MBLs including NDM-1, VIM-1, VIM-2, SPM-1 (Sao Paulo MBL-1) and IMP-1 and the non-clinically relevant model MBL *Bacillus cereus* (BcII).

The kinetic values determined were the means from at least three independent measurements. At least six different concentrations of the substrate or inhibitor were used to determinate the kinetic parameters (K$_M$, k$_{cat}$ and IC$_{50}$). Determination of the steady state kinetic parameters for the hydrolysis of different substrates ($K_M$ and $k_{cat}$) was performed by fitting the initial velocity data to the Michaelis-Menten equation using the software package Graph Prism 5.01. The $IC_{50}$ values were determined from the plot of activity (steady state rate) versus inhibitor concentration using the same software.

$IC_{50}$ values (concentration required to affect 50% inhibition of enzyme activity) were determined by preincubation of the appropriate amount of enzyme with the desired compound in the assay buffer for 10 min at r.t. prior to the initiation of the assay by the addition of the substrate. The compounds for inhibition study were prepared in 1 to 100 mM DMSO stock solutions. Additional tests verified that the low concentration of DMSO (0.5%) present in the reaction mixture had no inhibition effects.

isolates. All strains producing MBLs were confirmed as resistant to meropenem at the Clinical and Laboratory Standards Institute (U.S.A.) defined breakpoint of 8 μg/mL for *Enterobacteriace* (see Table 2 below). The minimum inhibitory concentration (MIC) of meropenem against wild-type and MBL producing *Escherichia coli* and *Klebsiella pneumoniae* strains was determined with and without increasing concentrations of ML302 or ML302F. Clinical and Laboratory Standards Institute. 2012. Methods for dilution antimicrobial susceptibility tests for bacteria that grow aerobically; 9th ed. Approved standard M07-A9. CLSI, Wayne, Pa.; and Clinical and Laboratory Standards Institute. 2012. Performance standards for antimicrobial susceptibility testing; 22nd informational supplement M100-S22. CLSI, Wayne, Pa.

TABLE 2

| Strain | Meropenem MIC (mg/L) in the absence of inhibitor | Meropenem MIC (mg/L) in the presence of inhibitor ML302 or ML302F at concentration stated | | | |
|---|---|---|---|---|---|
| | | 10 mg/L ML302/ ML302F | 25 mg/L ML302/ ML302F | 50 mg/L ML302/ ML302F | 100 mg/L ML302/ ML302F |
| *E. coli* 25722 (wt) | ≤0.25 | ≤0.25/≤0.25 | ≤0.25/≤0.25 | ≤0.25/≤0.25 | ≤0.25/≤0.25 |
| *K. pneumoniae* NCTC 5055 (wt) | ≤0.25 | ≤0.25/≤0.25 | ≤0.25/≤0.25 | ≤0.25/≤0.25 | ≤0.25/≤0.25 |
| *E. coli* MG1655 (IMP-1) | 32 | 0.5/4 | ≤0.25/4 | ≤0.25/2 | ≤0.25/0.5 |
| *K. pneumoniae* NCTC 5055 (IMP-1) | 32 | ≤0.25/4 | ≤0.25/0.5 | ≤0.25/0.5 | ≤0.25/≤0.25 |
| *K. pneumoniae* B19 (IMP-4) | 16 | 0.5/2 | ≤0.25/1 | ≤0.25/0.5 | ≤0.25/≤0.25 |
| *K. pneumoniae* A34 (VIM-4) | 128 | 32/64 | 8/32 | 4/32 | 4/16 |
| *E. coli* IR60 (NDM-1) | 16 | 8/16 | 8/16 | 4/8 | 2/8 |

Results are depicted in Table 1 below and in FIG. 1 which depicts the $IC_{50}$ curves for ML302, ML302F and the mixture of the two compounds against the panel of MBLs.

TABLE 1

| | $IC_{50}$ [μM] | | |
|---|---|---|---|
| MBL | ML302 | ML302F | ML302M |
| NDM-1 | 9.44 ± 1.44 | 1.05 ± 0.3 | 0.52 ± 0.18 |
| VIM-1 | 0.66 ± 0.25 | 0.44 ± 0.19 | 0.26 ± 0.13 |
| VIM-2 | 0.49 ± 0.18 | 0.30 ± 0.09 | 0.016 ± 0.004 |
| SPM-1 | 1.32 ± 0.62 | 1.76 ± 0.51 | 0.14 ± 0.04 |
| IMP-1 | 0.1749 ± 0.060 | 2.88E-3 ± 0.50 | 0.061 ± 0.017 |
| BcII | 0.50 ± 0.15 | 0.02 ± 0.07 | 0.56 ± 0.19 |

The $IC_{50}$ value for ML302 against VIM-2 obtained using this assay (498±18 nM) agrees well with the reported value of 548 nM (Spicer, T et al A Novel Beta-lactamase (BLA) Inhibitor in *Probe Reports from the NIH Molecular Libraries Program* (National Center for Biotechnology Information (US), Bethesda (Md.), 2010). Results against VIM-2 show signficantly higher potency for ML302F than for ML302. Further, the mixture of ML302F and ML302 shows higher potency than either compound alone.

Example 4: Cellular and Selectivity Studies

Further studies were carried out to determine if ML302F/ML302 potentiates β-lactam antibiotic activity in clinically derived strains containing IMP-1, IMP-4, VIM-4 or NDM-1, which are the most commonly observed MBLs in clinical There was no noticeable effect of either inhibitor at 100 μg/mL on *E. coli*/*K pneumoniae* growth, without meropenem, suggesting no direct toxicity. Synergy between ML302 and meropenem was observed for all MBL producing strains (see Table 2) with clinically relevant sensitivity (MIC<8 μg/mL) achieved at 50 μg/mL of inhibitor against VIM and NDM producers. In contrast, the lowest concentration of inhibitor tested (10 μg/mL) conferred meropenem sensitivity on IMP producers. For comparison, the SBL inhibitor Avibactam is typically used at 4 μg/mL to potentiate ceftazidime (Zhanel et al Drugs, 73 159-177 (2013). It is notable that the zinc-chelator MBL inhibitor Aspergillomarasmine A (King A. M. et al Nature 510, 503-506 (2014)) shows similar or better potentiating effect against VIM and NDM producing strains, but ML302 has a broader activity also targeting IMP producing strains. ML302F also displayed synergy with meropenem. Meropenem sensitivity was again observed for IMP producers at the lowest close tested (10 μg/mL), but the meropenem MICs observed in the presence of ML302F were up to 8-fold higher than the same ML302 concentration.

In a further study, antimicrobial activities of MEM and ML302F alone and in combination were assessed in-vitro against 31 VIM-producing clinical isolates. Synergy between MEM and ML302F was first confirmed in checkerboard assays against 7/8 isolates tested (FICI≤0.5). A MEM:ML302F ratio of 1:4 and 1:8 was found to be optimal resulting in a ≥4 fold reduction in the MIC of MEM. Thirty strains were either resistant (MIC>8 mg/L) or had reduced susceptibility (MIC≥4 mg/L) to MEM alone as judged by the European Committee on Antimicrobial Susceptibility (EUCAST) breakpoint criteria. One *K. pneumoniae* isolate harbouring blaVIM-1 was deemed susceptible (MIC 1 mg/L). Using a fixed 1:8 ratio of MEM:ML302F in-vitro susceptibility to carbapenems was increased in 22/31 (70%) of the isolates with 11 rendered susceptible (MIC≤2 mg/L)) or intermediate (MIC 4-8 mg/L). For 9 isolates, the MIC of MEM remained >8 mg/L. Results are set out in Table 3 below.

TABLE 3

Table 3: Minimum inhibitory concentrations (MICs) of meropenem (MEM) with and without ML302F (1:8) versus multidrug-resistant Gram-negative bacteria producing VIM carbapenemases.

| MBL | Isolate | MIC (mg/L) MEM | MEM + ML302F | FICI |
|---|---|---|---|---|
| VIM-1 | *K. pneumoniae* GR54 | 128 | 4 | 0.09 |
| VIM-1 | *K. pneumoniae* 177 | 1 | 1 | 1.02 |
| VIM-1 | *P.. stuartii* 67 | 8 | 1 | 0.14 |
| VIM-1 | *P. stuartii* 70 | 8 | 1 | 0.14 |
| VIM-2 | *P. aeruginosa* 30 | 64 | 8 | 0.25 |
| VIM-2 | *P. aeruginosa* 47 | 32 | 1 | 0.05 |
| VIM-2 | *P. aeruginosa* 50 | 32 | 8 | 0.38 |
| VIM-2 | *P. aeruginosa* GR57 | 32 | 4 | 0.19 |
| VIM-2 | *P. aeruginosa* GR58 | 32 | 8 | 0.38 |
| VIM-2 | *P. aeruginosa* GR62 | 32 | 8 | 0.38 |
| VIM-2 | *P. aeruginosa* GR64 | 32 | 4 | 0.19 |
| VIM-2 | *P. aeruginosa* 3 (13) | 64 | 8 | 0.25 |
| VIM-2 | *P. aeruginosa* 8 (13) | 128 | 16 | 0.38 |
| VIM-2 | *P. aeruginosa* 9 (13) | 128 | 16 | 0.38 |
| VIM-2 | *P. aeruginosa* 11 (13) | 32 | 2 | 0.09 |
| VIM-2 | *P. aeruginosa* 6 (14) | 128 | 16 | 0.38 |
| VIM-2 | *P. aeruginosa* 11 (14) | 128 | 32 | 0.75 |
| VIM-2 | *P. aeruginosa* 12 (14) | 128 | 32 | 0.75 |
| VIM-2 | *P. aeruginosa* 13 (14) | 32 | 16 | 0.75 |
| VIM-2 | *P. aeruginosa* 14 (14) | 64 | 2 | 0.06 |
| VIM-2 | *P. aeruginosa* 15 (14) | 64 | 16 | 0.5 |
| VIM-2 | *P. aeruginosa* 16 (14) | 64 | 16 | 0.5 |
| VIM-2 | *P. aeruginosa* 27 (14) | 64 | 16 | 0.5 |
| VIM-4 | *E. cloacae* 102 | 32 | 4 | 0.19 |
| VIM-4 | *E. coli* 98 | 16 | 2 | 0.16 |
| VIM-4 | *K. oxytoca* 95 | 32 | 8 | 0.38 |
| VIM-4 | *K. oxytoca* 126 | 32 | 4 | 0.19 |
| VIM-4 | *K. pneumoniae* 101 | 32 | 2 | 0.09 |
| VIM-4 | *K. pneumoniae* 120 | 16 | 2 | 0.25 |
| VIM-4 | *K. pneumoniae* 128 | 4 | 1 | 0.27 |
| VIM-4 | *K. pneumoniae* 196 | 16 | 1 | 0.08 |

Example 5: Selectivity Studies

To investigate the selectivity of ML302/ML302F for bacterial MBLs, activity was tested against TEM-1 (a Class A SBL), PBP-5 (penicillin-binding protein 5 or dacA) and PBP-6 (penicillin-binding protein 6, or dacC) from *E. coli*, hHAT (human histone acetyltransferase) and hHDAC (human histone deacetylase). TEM-1, PBP-5 and -6 and hHAT are known to be inhibited by rhodanines. Selectively against hACE-2 (Angiotensin converting enzyme 2) and hHAGH (Hydroxyacylglutathione hydrolase, human Glyoxalase II) was also tested.

Inhibition Studies for Penicillin Binding Proteins

The inhibition analyses were performed using the method previously described for PBP-3 (van Berkel, S. S. et al. Binding of (5 S)-penicilloic acid to penicillin binding protein 3. *ACS Chem. Biol.* 8, 2112-2116 (2013)). In brief: ML302 and ML302F were initially screened at a single concentration (100 µM) in duplicate. Inhibition of the PBP acylation rate by the chromogenic β-lactam Nitrocefin was determined by pre-incubation of the appropriate amount of enzyme (dacA 2 µM and dacC 6.8 µM, respectively) and inhibitor in the assay buffer (50 mM HEPES-NaOH buffer (pH 7.2) supplemented with 200 mM NaCl and 0.01% Triton 100) for 10 min. at r.t. prior to the initiation of the assay by the addition of nitrocefin (100 µM final concentration). The hydrolysis of Nitrocefin was monitored by following the variation in absorbance at 492 nm using 96 well flat bottom plates (UV-STAR Microplate (655801) or Greiner Bio-One). The experiments were performed using a PHERAstar FS—BMG Labtech microplate reader (using path length correction) at r.t. (24-25° C.). All enzymes and inhibitors were prepared in the assay buffer.

Inhibition Studies TEM-1

The inhibition analysis for TEM-1 was performed using the modified method that was previously described for MBLs.21 In brief: ML302 and ML302F were screened at a single concentration (100 µM) in duplicate. Inhibition was tested by pre-incubation of the appropriate amount of TEM-1 (1 nM final concentration) and ML302 or ML302F in the assay buffer (50 mM HEPES-NaOH buffer (pH 7.2) supplemented with 0.01% Triton 100) for 10 min. at r.t. prior to the initiation of the assay by the addition of FC5 ((6R, 7R)-8-Oxo-3-(((2-oxo-2H-chromen-7-yl)oxy)methyl)-7-(2-phenylacetamido)-5-thia-1-azabicyclo[4.2.0]oct-2-ene-2-carboxylic acid 5,5-dioxide)21 (10 µM final concentration). The hydrolysis of FC5 was monitored by following the variation on fluorescence reading (380 nm—excitation and 460 nm—emission) using 384 well flat bottom plates (Greiner Bio-One). The experiments were performed on a PHERAstar FS-BMG Labtech microplate reader at r.t. (24-25° C.). All enzymes and inhibitors were prepared in the assay buffer.

Inhibition Studies for hHAT, HDAC, hACE-2 and hHAGH

The inhibition analyses for human histone acetyltransferases (HAT), HDAC hHDAC (human histone deacetylase), hACE-2 (Angiotensin converting enzyme 2) and hHAGH (Hydroxyacylglutathione hydrolase, human Glyoxylase II) were performed using the commercially available HAT Assay Kit (Active Motif, catalogue No. 56100 (2009)), hHDAC (Active Motif, catalogue No. 56200 (2013)), hACE-2 (ACE-2 (R&D Systems) and hHAGH ((R&D Systems).

hACE 2 Assay (R&D systems):

Materials:

Assay Buffer: 75 mM Tris, 1 M NaCl, pH 7.5

Recombinant Human ACE-2 (rhACE-2) (Catalog #933-ZN)

Substrate: MCA-Tyr-Val-Ala-Asp-Ala-Pro-Lys(DNP)-OH (Catalog # ES007), 10 mM stock in DMSO F16 Black Maxisorp Plate (Nunc, Catalog #475515)

Fluorescent Plate Reader (Model: SpectraMax Gemini EM by Molecular Devices) or equivalent Assay:

1. Dilute rhACE-2 to 0.2 ng/µL in Assay Buffer.

2. Dilute Substrate to 40 µM in Assay Buffer.

3. Load in a black well plate 50 µL of 0.2 ng/rhACE-2, and start the reaction by adding 50 µL of 40 µM Substrate. As a control load 50 IJL of 40 IJM Substrate with 50 µL of Assay Buffer.

4. Read at excitation and emission wavelengths of 320 nm and 405 nm (top read), respectively in kinetic mode for 5 minutes.

5. Calculate specific activity:

$$\text{Specific Activity}_{(pmol/min/{\mu}g)} = \left( \frac{\text{Adjusted } V\max^*(OD/\min) \times \text{well volume}(L) \times 10^{12} \text{ pmol/mol}}{ext.coeff^{**}(M^{-1}\text{cm}^{-1}) \times} \right)$$
$$\text{path } corr.^{***}(\text{cm}) \times \text{amount of enzyme}(pg)$$

*Adjusted for Substrate Blank

**Derived using calibration standard MCA-Pro-Leu-OH (Bachem, Catalog #M-1975)

Final Assay Conditions
Per Well:
  rhACE-2: 0.010 µg
  Substrate: 20 µM
hAGHAssay (R&D Systems)
Materials:
  Assay Buffer: 50 mM Tris, 250 mM NaCl, pH 7.5
  Recombinant Human Glyoxalase II (rhGlyoxalase II) (Catalog #5944-GO)
  Substrate: S-Lactoylglutathione (Sigma, Catalog # L7140), 100 mM stock in deionized water
  5, 5'-dithiobis(2-nitrobenzoic acid) (DTNB) (Sigma, Catalog # D8130), 10 mM stock in DMSO
  96-well Clear Plate (Costar, Catalog #92592)
  Plate Reader (Model: SpectraMax Plus by Molecular Devices) or equivalent
Assay:
1. Dilute rhGlyoxalase II to 0.4 ng/µL in Assay Buffer.
2. Dilute Substrate to 2 mM in Assay Buffer with 400 IJM DTNB to form Substrate Mixture.
3. Load 50 µL of 0.4 ng/µL rhGlyoxalase II into a plate and start the reaction by loading 50 µL of Substrate Mixture. Include a Substrate Blank containing 50 µL of Assay Buffer and 50 µL of Substrate Mixture.
4. Read at 405 nm (absorbance) in kinetic mode for 5 minutes.
5. Calculate specific activity:

$$\text{Specific Activity}_{(pmol/min/{\mu}g)} = \left( \frac{\text{Adjusted } V\max^*(OD/\min) \times \text{well volume}(L) \times 10^{12} \text{ pmol/mol}}{ext.coeff^{**}(M^{-1}\text{cm}^{-1}) \times} \right)$$
$$\text{path } corr.^{***}(\text{cm}) \times \text{amount of enzyme}(pg)$$

*Adjusted for Substrate Blank

**Using the extinction coefficient 13260 $M^{-1}\text{cm}^{-1}$

***Using the path correction 0.320 cm

Note: the output of many spectrophotometers is in mOD.
Final Assay Conditions Per Well:
rhGlyoxalase II: 0.020 pg
S-Lactoylglutathione: 1 mM
DTNB: 200 µM Results of each assay are set out in Table 4 below.

TABLE 4

| Entry | Enzyme | ML302 RA [%] | ML302F | Control RA [%]a |
|---|---|---|---|---|
| 1 | TEM-1 | 98.6 ± 7.1/N.I. | 99.6 ± 3.1/N.I. | Clavulanic acid |
| 2 | PBP5 (dacA) from E. coli | 104.6 ± 5.7 | 99.2 ± 6.4/N.I. | Piperacillin |
| 3 | PBP6 (dacC) from E. coli | 97.7 ± 3.8/N.I. | 114 ± 19.6/N.I. | Piperacillin |
| 4 | hHAT | 93 ± 15/N.I. | 85 ± 9/N.I. | Anacardic acid |
| 5 | hHDAC | 108 ± 3/N.I. | 116 ± 7/N.I. | Trichostatin |
| 6 | hACE-2 | 73 ± 9 | 99 ± 4/N.I. | EDTA |
| 7 | hGlyoxylase II | 98 ± 3/N.I. | 95 ± 6/N.I. | EDTA |

N.I.—not inhibited;
RA ≤ 1% at 100 µM

Only in the case of hACE-2 did we observe inhibition (~75% residual activity at 100 µM) by ML302 but not by ML302F. For all the other tested enzymes we did not observe any substantial inhibition (Table.3). Overall these results suggest that the ML302F/ML302 or ML302M are selective for MBL inhibition.

Example 6—Toxicity Assays

The in vivo toxicity of ML302F was assessed in the *Galleria mellonella* wax moth larvae model using a simple live dead ranking. Increasing doubling concentrations of ML302F (0 to 80 mg/Kg) were administered in 10 µl injections directly into the hemocoel of ten larvae before incubation at 37° C. for 96 h. Larvae were scored for mellonisation and movement every 24 h, as live or dead. Larvae for all *G. mellonella* assays were purchased from Livefood UK Ltd (Somerset, UK).

ML302F was non-toxic when administered to *G. mellonella* by injection at closes up to 80 mg/kg (100% survival of all larvae at 96 hrs).

Example 7—G. Mellonella Virulence Assay

The bacterial inocula required for staggered killing (50% lethal dose [LD50) of *G. mellonella* by VIM producing isolates over 96 h was determined using 10 larvae inoculated with overnight cultures of *E. coli* EC98, *K. pneumoniae* KP120 and *P. aeruginosa* PA GR57. Tenfold serial dilutions were made from washed cultures, diluted in PBS and administered in 10 µl injections at final concentrations of 101-106 CFU/larvae and incubated at 37° C. for 96 h. Larvae were scored as live or dead every 24 h.

The inoculum required for staggered killing of >50% of larvae by carbapenem resistant strains over 96 h varied by species. The LD50 was <101, 105 and 104 CFU/larvae for *P. aeruginosa* GR57, *E. coli* 98 and *K. pneumoniae* respectively.

Example 8—MEM/ML302F Treatment Assays

The activity of MEM and ML302F alone and in combination were assessed using 16 *G. mellonella* larva as described by M. Hornsey and D. W. Wareham (*Antimicrob. Agents Chemother.*, 2011, 55(7), 3534-3537). Larvae were inoculated with *P. aeruginosa* GR57, *E. coli* EC98 and *K. pneumoniae* KP120. In combination therapies, a fixed ratio (1:8) of MEM:ML302F containing 0.6 mg/Kg of MEM8 and 4.8 mg/Kg of ML302F was administered in 10 µL injections to infected larvae. PBS injections (10 µL) were used as both controls for no antimicrobial therapy and inoculation injury. Larvae were scored for survival over 96 hrs and kill curves analysed by the log-rank test for trend. Relative risk (RR) of survival between the different treatment arms was calculated using Fisher's exact test with, two-tailed P-values of <0.05 considered statistically significant.

Figure 2:
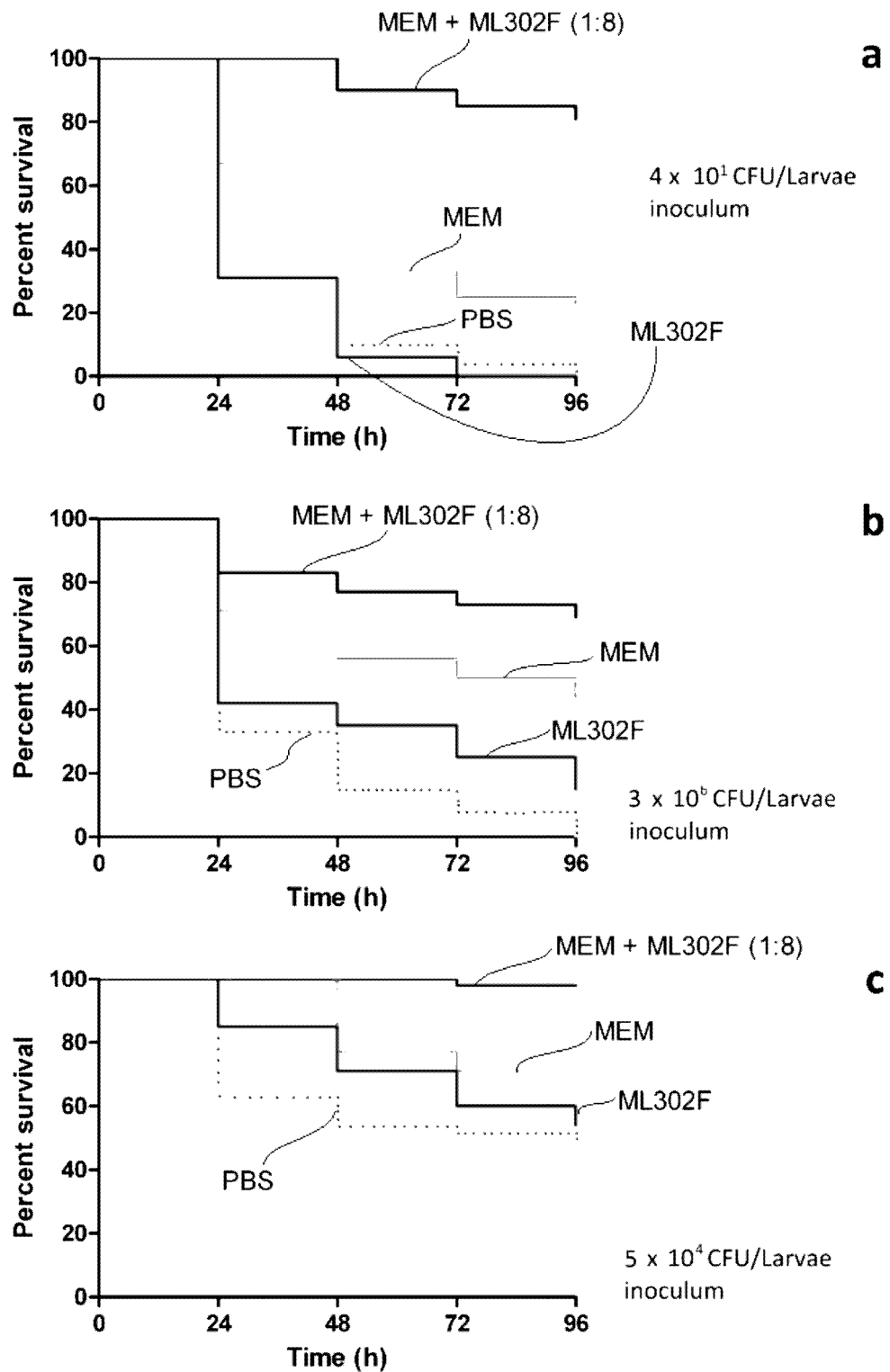
FIG. 2 provides the results of the treatment assays described in Example 8 as plots a b and c. In plot a, the uppermost line represents results of treatment with MEM in combination with ML302F, the second-from-top line represents the results of treatment with MEM, the second-from-bottom line represents the results of treatment with PBS, and the bottom line represents the results of treatment with ML302F. In plots b and c, the uppermost line represents results of treatment with MEM in combination with ML302F, the second-from-top line represents the results of treatment with MEM, the second-from-bottom line represents the results of treatment with ML302F, and the bottom line represents the results of treatment with PBS.

Results are given in FIG. 2 and show that survival of ML302F (4.8 mg/kg) treated larvae was similar to those given PBS for the treatment of PA GR57, EC 98 and KP 120 infections. Monotherapy with MEM (0.6 mg/kg) was superior to either PBS and ML302F (P<0.0001) but % survival was only 44%, 23% and 69% versus strains EC 98, PA GR57 and KP 120 respectively. The addition of ML302F to MEM significantly improved the survival of infected larva (P<0.0001) compared to MEM alone, with survival rates of 69% (EC 98), 81% (PA GR57) and 98% (KP 120) at 96 (FIG. 2) and a relative risk for MEM-ML302F versus MEM of 0.64, 0.28 and 0.70 for these isolates.

The invention claimed is:

1. A method for the treatment of bacterial infection in a subject by inhibiting bacterial metallo-beta-lactamase activity in the subject, which method comprises administering to the subject an effective amount of a compound which is a thienolate of formula (I) or a pharmaceutically acceptable salt thereof, and further administering to the subject an effective amount of a β lactam antibiotic agent:

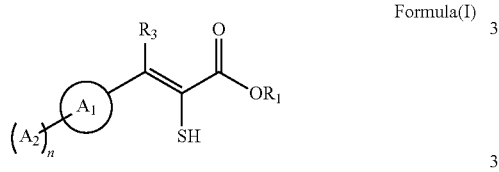

Formula(I)

wherein
R1 is H or a C1 to C4 alkyl group;
R3 is H, halogen, C1 to C4 alkyl, OH, C1 to C4 alkoxy, C2 to C4 alkenyl, or —NR4R5;
Ring A1 is phenyl which is unsubstituted or substituted with from 1 to 4 substituents selected from halogen, OH, —NR4R5, CN, NO2, —C(O)R4, —C(O)OR4, —C(O)NR4R5, —S(O)R4, C1 to C4 alkyl, C1 to C4 alkoxy or C2 to C4 alkenyl groups which are themselves unsubstituted or substituted with from 1 to 3 further unsubstituted substituents selected from halogen, OH, —NR4R5 or C1 to C4 alkoxy;
n is 0 or 1;
Ring A2 is phenyl which is unsubstituted or substituted with from 1 to 4 substituents selected from halogen, OH, —NR4R5, CN, NO2, —C(O)R4, —C(O)OR4, —C(O)NR4R5, —S(O)R4, C1 to C4 alkyl, C1 to C4 alkoxy or C2 to C4 alkenyl groups which are themselves unsubstituted or substituted with from 1 to 3 further unsubstituted substituents selected from halogen, OH, —$NR^4R^5$ or $C_1$ to $C_4$ alkoxy; and
$R^4$ and $R^5$ each independently represent H or $C_1$ to $C_4$ alkyl.

2. The method according to claim 1, wherein $R^1$ is hydrogen, methyl or ethyl.

3. The method according to claim 1, wherein $R^3$ is hydrogen.

4. The method according to claim 1, wherein Ring A1 is phenyl which is unsubstituted or substituted with from 1 to 4 unsubstituted substituents selected from halogen, OH, NO2, —$NR^4R^5$, —$CF_3$, —$C(O)R^4$, —$C(O)OR^4$, —$C(O)$ $NR^4R^5$, —$S(O)R^4$, $C_1$ to $C_4$ alkyl, $C_1$ to $C_4$ alkoxy or $C_2$ to $C_4$ alkenyl, wherein $R^4$ and $R^5$ each independently represent hydrogen, methyl or ethyl.

5. The method according to claim 1, wherein Ring A1 is phenyl, A1 being unsubstituted or substituted with 1, 2 or 3 substituents selected from halogen, NO2, methyl, methoxy, —$CO_2R^4$, —$COR^4$, or —$S(O)R^4$, wherein $R^4$ represents hydrogen or $C_1$-$C_2$ alkyl.

6. The method according to claim 1, wherein ring A1 carries at least two substituents in the diortho positions relative to the thioenolate group.

7. The method according to claim 1, wherein Ring A2 is phenyl, A2 being unsubstituted or substituted with 1, 2 or 3 unsubstituted substituents selected from halogen, e.g. fluorine or chlorine, OH, —NH2, methyl or methoxy.

8. The method according to claim 1, wherein
$R^1$ is hydrogen, methyl or ethyl;
$R^3$ is hydrogen, halogen, methyl, ethyl, OH, methoxy or ethoxy;
Ring A1 is phenyl, wherein the ring A1 is unsubstituted or substituted with from 1 to 4 unsubstituted substituents selected from halogen, OH, NO2, —$NR^4R^5$, —$CF_3$, —$C(O)R^4$, —$C(O)OR^4$, —$C(O)NR^4R^5$, —$S(O)R^4$, $C_1$ to $C_4$ alkyl, $C_1$ to $C_4$ alkoxy or $C_2$ to $C_4$ alkenyl;
Ring A2 is phenyl, wherein the ring A2 is unsubstituted or substituted with from 1 to 4 unsubstituted substituents selected from halogen, OH, NO2, —$NR^4R^5$, —$CF_3$, —$C(O)R^4$, —$C(O)OR^4$, —$C(O)NR^4R^5$, —$S(O)R^4$, $C_1$ to $C_4$ alkyl, $C_1$ to $C_4$ alkoxy or $C_2$ to $C_4$ alkenyl; and
$R^4$ and $R^5$ each independently represent hydrogen, methyl or ethyl.

9. The method according to claim 1, wherein the compound is a thioenolate of formula (IA) or pharmaceutically acceptable salt thereof:

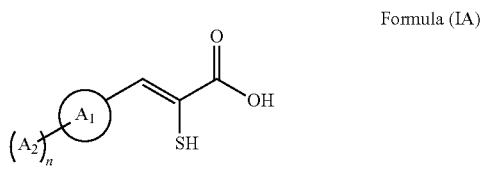

Formula (IA)

wherein
Ring A1 is phenyl, A1 being unsubstituted or substituted with 1, 2 or 3 substituents selected from halogen, NO2, methyl, methoxy, —$CO_2R^4$, —$COR^4$, or —$S(O)R^4$, wherein $R^4$ represents hydrogen or $C_1$-$C_2$ alkyl;
n is 0 or 1;
Ring A2 is phenyl, A2 being unsubstituted or substituted with 1, 2 or 3 unsubstituted substituents selected from halogen, OH, —NH2, methyl or methoxy.

10. The method according to claim 1, wherein the compound is (Z)-2-mercapto-3-(2,3,6-trichlorophenyl)acrylic acid or a pharmaceutically acceptable salt thereof.

11. The method of claim 1, which is a method of potentiating the activity of the β lactam antibiotic agent.

12. The method of claim 1, wherein the β lactam antibiotic agent is a carbapenem, ureidopenicillin, carbacephem or cephalosporin.

13. The method of claim 1, wherein the β lactam antibiotic agent is selected from temocillin, piperacillin, cefpodoxime, ceftazidime, cefotaxime, ceftriaxone, meropenem, faropenem, imipenem, loracarbef, ceftobiprole or ceftaroline.

14. The method of claim 1, wherein the bacterial infection is caused by *E. coli* or *K. Pneumoniae*.

15. The method of claim 1, which further comprises administering to the subject an effective amount of a compound which is rhodanine of formula (II) or a pharmaceutically acceptable salt thereof:

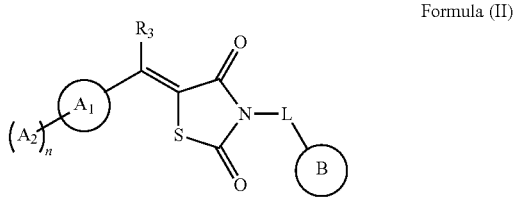

Formula (II)

wherein $R^3$ is H, halogen, $C_1$ to $C_4$ alkyl, OH, $C_1$ to $C_4$ alkoxy, $C_2$ to $C_4$ alkenyl, or —$NR^4R^5$;

Ring A1 is phenyl which is unsubstituted or substituted with from 1 to 4 substituents selected from halogen, OH, —$NR^4R^5$, CN, $NO_2$, —$C(O)R^4$, —$C(O)OR^4$, —$C(O)NR^4R^5$, —$S(O)R^4$, $C_1$ to $C_4$ alkyl, $C_1$ to $C_4$ alkoxy or $C_2$ to $C_4$ alkenyl groups which are themselves unsubstituted or substituted with from 1 to 3 further unsubstituted substituents selected from halogen, OH, —$NR^4R^5$ or $C_1$ to $C_4$ alkoxy;

n is 0 or 1;

Ring A2 is phenyl which is unsubstituted or substituted with from 1 to 4 substituents selected from halogen, OH, —$NR^4R^5$, CN, $NO_2$, —$C(O)R^4$, —$C(O)OR^4$, —$C(O)NR^4R^5$, —$S(O)R^4$, $C_1$ to $C_4$ alkyl, $C_1$ to $C_4$ alkoxy or $C_2$ to $C_4$ alkenyl groups which are themselves unsubstituted or substituted with from 1 to 3 further unsubstituted substituents selected from halogen, OH, —$NR^4R^5$ or $C_1$ to $C_4$ alkoxy;

L is a linker of formula -$(Alk^1)_p$-$(Het)_q$-$(Alk^2)_r$-, wherein $Alk^1$ and $Alk^2$ independently represent $C_1$ to $C_4$ alkylene and Het represents —O—, —S—, —$NR^4$—, —C(O)—, —C(O)O— or —$C(O)NR^4$—, and p, q and r are each independently 0 or 1;

Ring B is selected from a 5- to 6-membered carbocyclic group, pyridinyl, pyrazinyl or morpholinyl, each of which is unsubstituted or substituted with 1, 2 or 3 substituents selected from halogen, OH, $NO_2$, —$NR^4R^5$, —$C(O)OR^4$, $C_1$ to $C_4$ alkyl, $C_1$ to $C_4$ alkoxy or $C_2$ to $C_4$ alkenyl groups which are themselves unsubstituted or substituted with from 1 to 3 further unsubstituted substituents selected from halogen, OH, —$NR^4R^5$ or $C_1$ to $C_4$ alkoxy; and $R^4$ and $R^5$ each independently represent H or $C_1$ to $C_4$ alkyl.

16. The method of claim 15, wherein the compound of formula (I) is a thioenolate of formula (IA) or pharmaceutically acceptable salt thereof:

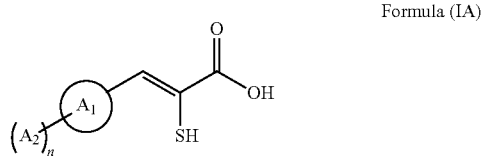

Formula (IA)

wherein

Ring A1 is phenyl, A1 being unsubstituted or substituted with 1, 2 or 3 substituents selected from halogen, $NO_2$, methyl, methoxy, —$CO_2R^4$, —$COR^4$, or —$S(O)R^4$, wherein $R^4$ represents hydrogen or $C_1$-$C_2$ alkyl;

n is 0 or 1;

Ring A2 is phenyl, A2 being unsubstituted or substituted with 1, 2 or 3 unsubstituted substituents selected from halogen, OH, —$NH_2$, methyl or methoxy; and the compound of formula (II) is a rhodanine of formula (IIA) or a pharmaceutically acceptable salt thereof:

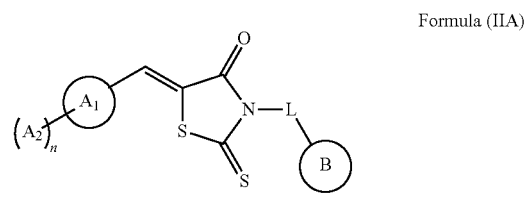

Formula (IIA)

wherein

Ring A1 is phenyl, A1 being unsubstituted or substituted with 1, 2 or 3 substituents selected from halogen, $NO_2$, methyl, methoxy, —$CO_2R^4$, —$COR^4$, or —$S(O)R^4$, wherein $R^4$ represents hydrogen or $C_1$-$C_2$ alkyl;

n is 0 or 1;

Ring A2 is phenyl, A2 being unsubstituted or substituted with 1, 2 or 3 unsubstituted substituents selected from halogen, OH, —$NH_2$, methyl or methoxy, wherein A2 is preferably unsubstituted;

L is a linker of formula —$(CH_2)_p$-(Het)-$(CH_2)_r$—, wherein Het represents —O—, —NH—, —C(O)—, —C(O)O— or —C(O)NH—, and p and r are each independently 0 or 1; preferably L is —$CH_2$—CO—NH—; and B is selected from cyclohexyl, pyridinyl, pyrazinyl or morpholinyl, wherein B is unsubstituted or substituted with 1 or 2 unsubstituted substituents selected from halogen, OH, —$NH_2$, methyl or methoxy.

17. A method for the treatment of bacterial infection in a subject by inhibiting bacterial metallo-beta-lactamase activity in the subject, which method comprises administering to the subject an effective amount of (Z)-2-mercapto-3-(2,3,6-trichlorophenyl)acrylic acid or a pharmaceutically acceptable salt thereof, and further administering to the subject an effective amount of a β lactam antibiotic agent; and further comprises administering to the subject an effective amount of (Z)-N-(4-methylpiperazin-1-yl)-2-(4-oxo-2-thioxo-5-(2,3,6-trichlorobenzylidene)thiazolidin-3-yl)acetamide or a pharmaceutically acceptable salt thereof.

18. The method of claim 15, which is a method of potentiating the activity of the β lactam antibiotic agent.

19. The method of claim 15, wherein the β lactam antibiotic agent is a carbapenem, ureidopenicillin, carbacephem or cephalosporin.

20. The method of claim 15, wherein the β lactam antibiotic agent is selected from temocillin, piperacillin, cefpodoxime, ceftazidime, cefotaxime, ceftriaxone, meropenem, faropenem, imipenem, loracarbef, ceftobiprole or ceftaroline.

21. The method of claim 15, wherein the bacterial infection is caused by *E. coli* or *K. pneumoniae*.

* * * * *